(12) United States Patent
Wei

(10) Patent No.: US 7,585,647 B2
(45) Date of Patent: Sep. 8, 2009

(54) NUCLEIC ACID ENCODING RECOMBINANT INTERFERON

(76) Inventor: Guangwen Wei, No. 8, Yusa Road, Chengdu, Sichuan 610017 (CN)

( * ) Notice: Subject to any disclaimer, the term of this patent is extended or adjusted under 35 U.S.C. 154(b) by 309 days.

(21) Appl. No.: 10/928,956

(22) Filed: Aug. 26, 2004

(65) Prior Publication Data

US 2005/0169885 A1    Aug. 4, 2005

Related U.S. Application Data

(60) Provisional application No. 60/498,449, filed on Aug. 28, 2003.

(30) Foreign Application Priority Data

| Mar. 5, 2004 | (IN) | ................ 279/MUM/2004 |
| Mar. 5, 2004 | (IN) | ................ 280/MUM/2004 |

(51) Int. Cl.
  C12P 21/04    (2006.01)
  C07H 21/04    (2006.01)
(52) U.S. Cl. .................. 435/69.51; 536/23.52
(58) Field of Classification Search .......... None
  See application file for complete search history.

(56) References Cited

U.S. PATENT DOCUMENTS

| 4,462,940 | A * | 7/1984 | Hanisch et al. ............. 530/351 |
| 4,672,108 | A | 6/1987 | Kung et al. |
| 4,681,930 | A | 7/1987 | Kung et al. |
| 4,695,623 | A | 9/1987 | Stabinsky |
| 4,897,471 | A | 1/1990 | Stabinsky |
| 5,372,808 | A | 12/1994 | Blatt et al. |
| 5,441,734 | A | 8/1995 | Reichert et al. |
| 5,602,232 | A | 2/1997 | Reichert et al. |
| 5,710,027 | A | 1/1998 | Hauptmann et al. |
| 5,874,304 | A | 2/1999 | Zolotukhin et al. |
| 5,972,331 | A | 10/1999 | Reichert et al. |
| 5,980,884 | A | 11/1999 | Blatt et al. |
| 6,087,478 | A | 7/2000 | Vinkemeier et al. |
| 6,114,145 | A | 9/2000 | Olsen et al. |
| 6,532,437 | B1 | 3/2003 | Clardy et al. |
| 6,546,074 | B1 | 4/2003 | Blundell et al. |
| 6,579,695 | B1 | 6/2003 | Lambalot et al. |
| 7,364,724 | B2 | 4/2008 | Wei et al. |
| 2004/0115169 | A1 | 6/2004 | Wolfe et al. |
| 2004/0202641 | A1* | 10/2004 | Wei et al. ................... 424/85.5 |

FOREIGN PATENT DOCUMENTS

| AU | 2003248419 | | 11/2003 |
| CN | 1099799 | A | 3/1995 |
| CN | 1120846 | A | 4/1996 |
| CN | 1186120 | A | 7/1998 |
| CN | 1062565 | C | 2/1999 |
| CN | 1217660 | A | 5/1999 |
| CN | 1256148 | A | 6/2000 |
| CN | 1062565 | C | 2/2001 |
| CN | 1291198 | A | 4/2001 |
| CN | 1375502 | A | 10/2002 |
| CN | 1384116 | A | 12/2002 |
| CN | 1098103 | C | 1/2003 |
| CN | 1478545 | A | 3/2004 |
| DE | 4329756 | | 3/1995 |
| EP | 0083734 | B1 | 12/1982 |
| EP | 422697 | A | 4/1991 |
| EP | 0777495 | B1 | 10/1995 |
| EP | 0736303 | B1 | 3/1996 |
| EP | 1371373 | A1 | 12/2003 |
| WO | WO 8304053 | | 11/1983 |
| WO | WO 9321229 | | 10/1993 |
| WO | WO 94/19373 | | 9/1994 |
| WO | WO 97/27866 | | 8/1997 |
| WO | WO 97/27886 | | 8/1997 |
| WO | WO 99/40117 | | 8/1999 |
| WO | WO 01/35987 | A1 | 5/2001 |
| WO | WO 02080958 | | 10/2002 |
| WO | WO 2005/021777 | A2 | 3/2005 |
| WO | WO 2005/034853 | A2 | 4/2005 |
| WO | WO 2006/134497 | A2 | 12/2006 |

OTHER PUBLICATIONS

Ausubel F.M. et al. Analysis of Proteins. In Short Protocols in Molecular Biology. 4$^{th}$ Ed. 1999. p. 10-1-10-8.*
Cao Hongpeng, Tao Peizhen. Effect of Anti-HBV of 6 Drugs Include Lamividine. Natl Med J China, 2001,81(16):1004-1007.
Fei Junhua, Qin Laiyin, Fan Guiling, et al. Clinical Observation of Effect on Treatment of Chronic Hepatitis B by a Combination of Interferon ? and Lamividine. Shandong Medical Journal, 1999,39(11): 3-4.
Gao Yuanfu, Liu Guanglin, Xia Zhengkun, et al. Treatment of hepatitis virus related pediatric nephritis with IFN-?. Academic Journal of Jinlin Hospital, 1999,12(1):24-26.
Lei Binjun, Lu Yuhong, Qiu Yanqiu, et al. Observation on Clinical Treatment of Chronic Hepatitis B by Purified Human Leucocyte Interferon- ?. Chinese Journal of Practical Internal Medicine, 1995,15(3):155-157.
Lang Zhenwei, Han Honglei, Xu Dejun, et al. Observation on Serology and Histology of Patients with Chronic Hepatitis B after Interferon Treatment. Chin J Infet Dis., 2002,20(2):97-100.
Wang Xiangye, Li Xuegang. Comparing Effect of Three Drugs on Turning HBeAg to Negative. Qianwei Medical Journal, 1994,11(4):197-198.
PCT Notification of Transmittal of International Preliminary Report on Patentability for Huiyangtech (USA) Inc., Int'l Application No. PCT/US04/28068, Filed Aug. 26, 2004, Dated May 13, 2005.

(Continued)

*Primary Examiner*—Robert Landsman
*Assistant Examiner*—Bruce D. Hissong
(74) *Attorney, Agent, or Firm*—Law Offices of Albert Wai-Kit Chan, PLLC

(57) ABSTRACT

This invention provides a recombinant super-compound interferon or an equivalent thereof with changed spatial configuration. The super-compound interferon possesses antiviral or anti-tumor activity and, therefore, is useful in preventing and treating viral diseases and cancers. This invention also provides an artificial gene which codes for the super-compound interferon or its equivalent. Finally, this invention provides methods for producing recombinant super-compound interferon or its equivalent and various uses of said interferon.

8 Claims, 17 Drawing Sheets

OTHER PUBLICATIONS

Figure 3:
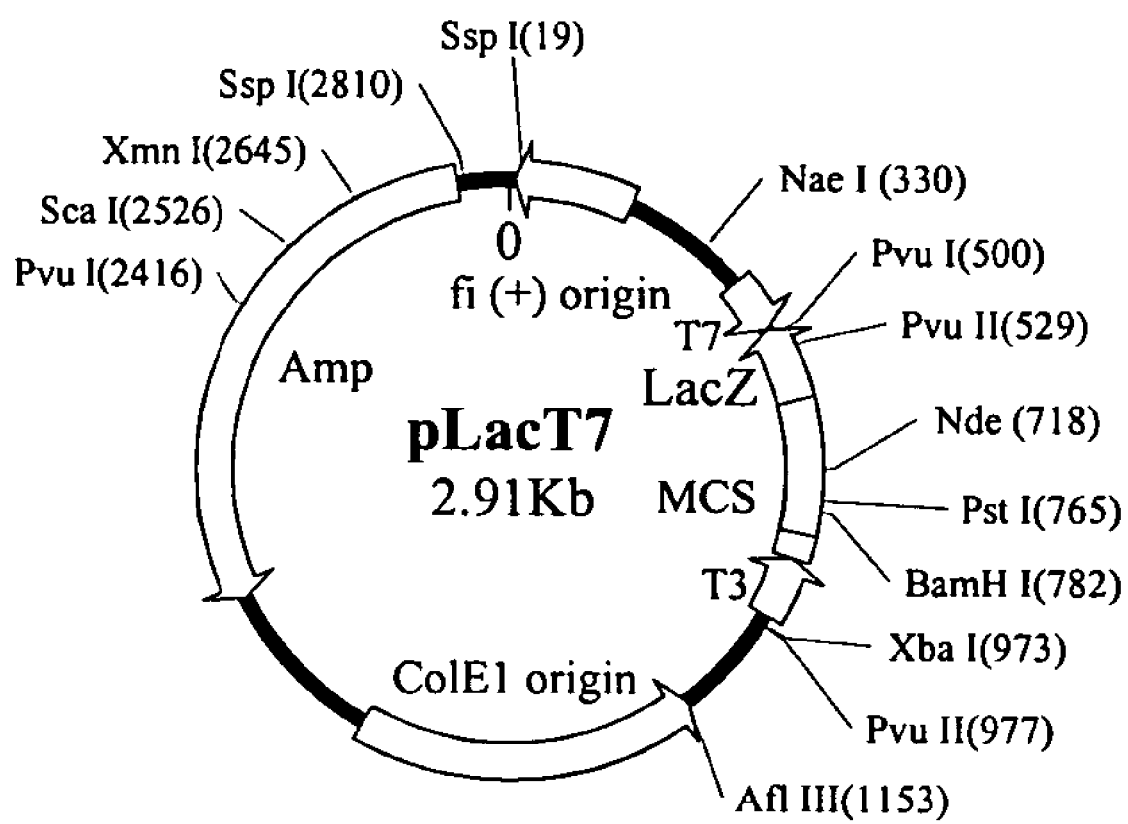

EPO Supplementary European Search Report, Application No. EP 02702211, Filed Feb. 28, 2002, Date of completion of the search: Feb. 23, 2005.

Apeler H, et al. "Expression of natural and synthetic genes encoding herpes simplex virus 1 protease in *Escherichia coli* and purification of the protein", European Journal Of Biochemistry / Febs. Aug. 1, 1997, vol. 247, No. 3, Aug. 1, 1997, pp. 890-895, XP002318941, ISSN: 0014-2956.

Guzman Luz-Maria, et al. "Tight regulation, modulation, and high-level expression by vectors containing the arabinose P-BAD promoter", Journal of Bacteriology, vol. 177, No. 14, 1995, pp. 4121-4130, XP002121022, ISSN: 0021-9193.

Huang Wanzhi, et al. "Use of the arabinosa pbad promoter for tightly regulated display of proteins on bacteriophage", Gene (Amsterdam), vol. 251, No. 2, Jun. 27, 2000, pp. 187-197, XP004206676, ISSN: 0378-1119.

Written Opinion of the International Searching Authority for PCT/US04/28068, filed Aug. 26, 2004 for Huiyangtech (USA) Inc., dated Mar. 4, 2005.

International Search Report for PCT/US04/28068, filed Aug. 26, 2004 for Huiyangtech (USA) Inc., dated Mar. 4, 2005.

Day, et al., "Engineered Disulfide Bond Greatly Increases Specific Activity of RecombinNT Murine Interferon-beta", Journal of Interferon Res, vol. 12, pp. 139-143 (1992).

Nasoff, et al., "High-Level Expression of Human Genes in *E. coli*", Expression, vol. 6, No. 2, pp. 10-11 (1999).

U.S. Appl. No. 10/650,365, filed Aug. 28, 2003, Guangwen Wei.
U.S. Appl. No. 10/928,474, filed Aug. 26, 2004, Guangwen Wei.
U.S. Appl. No. 10/927,975, filed Aug. 26, 2004, Guangwen Wei.
U.S. Appl. No. 11/077,813, filed Mar. 10, 2005, Guangwen Wei.

Nasoff, M, "High-level expression of human genes in *E. coli*" Expressions. 1999. vol. 6.2, p. 10-11.

Notification of Transmittal of International Preliminary Report on Patentability (Chapter II of the Patent Cooperation Treaty) for PCT/US04/28067 for Huiyangtech (USA), Inc., Dated Mar. 5, 2007.

Canadian Office Action for Sichuan Biotechnolgy Research Center, Canadian Application No. 2,439,503, Filed Aug. 27, 2003, Dated Apr. 21, 2008.

Chinese First Notification of Examination for Sichuan Biological Research Center, Chinese Application No. 01104367.9, Filed Feb. 28, 2001, Dated Apr. 18, 2003.

Chinese Second Notification of Examination for Sichuan Biological Research Center, Chinese Application No. 01104367.9, Filed Feb. 28, 2001, Dated Oct. 17, 2003.

Chinese Third Notification of Examination for Sichuan Biological Research Center, Chinese Application No. 01104367.9, Filed Feb. 28, 2001, Dated Jan. 2, 2004.

Chinese Fourth Notification of Examination for Sichuan Biological Research Center, Chinese Application No. 01104367.9, Filed Feb. 28, 2001, Dated Jun. 4, 2004.

Chinese Decision About Rejection for Sichuan Biological Research Center, Chinese Application No. 01104367.9, Filed Feb. 28, 2001, Dated Nov. 12, 2004.

Chinese Decision About the Reexamination for Sichuan Biological Research Center, Chinese Application No. 01104367.9, Filed Feb. 28, 2001, Dated Oct. 26, 2005.

Chinese Notification of Patent for Invention for Sichuan Biological Research Center, Chinese Application No. 01104367.9, Filed Feb. 28, 2001, Dated Oct. 26, 2005.

European Supplemental Search Report for Huiyangtech (USA), Inc., Application No. EP 04809634.1, Filed Mar. 26, 2006, Dated Jun. 17, 2008. Date of Completing of the Search: Jun. 10, 2008.

European Supplemental Search Report for Huiyangtech (USA), Inc., Application No. EP 04782529.4, Filed Mar. 24, 2006, Dated Jun. 17, 2008, Date of Completing of the Search: Jun. 3, 2008.

Japanese Notification of Reasons of Refusal for Sichuan Biotechnology Research Center, Japanese Application No. 2002-578997, Filed Aug. 28, 2003, Dated Jun. 17, 2008.

Singapore Certificate of Grant of Patent for Sichuan Biotechnology Research Center, Singapore Application No. 2003-04969, Filed Aug. 28, 2003, Dated Nov. 30, 2005.

Singapore Written Opinion for Huiyangtech (USA), Inc., Singapore Application No. 200601204-1, Filed Feb. 23, 2006, Dated Apr. 29, 2008.

Taiwanese Office Action for Sichuan Biotechnology Research Center, Taiwanese Application No. 92,123,846, Filed Aug. 28, 2003, Dated Aug. 30, 2006.

Taiwanese Formal Rejection for Sichuan Biotechnology Research Center, Taiwanese Application No. 92,123,846, Filed Aug. 28, 2003, Dated Dec. 11, 2006.

Duan et al., "Anti-SARS Virus Activities of Different Recombinant Human Interferons in Cell Culture System," Chinese J. Clin. Virol. 2003, 17(3):205-208.

Infergen (Interferon alfacon-1) Product Sheet, Amgen, Inc., Issue Date: Nov. 30, 1998.

pBAD Expression System, "Tightly Controlled Bacterial Protein Expression," Invitrogen Corp. Publication, 2002.

pBAD/HisA, B, and C; pBAD/Myc-HisA, B, and C, Version F, "Vectors for Dose-Dependent Expression of Recombinant Proteins Containing N- or C-terminal 6x His Tags in *E. coli*," Catalog Nos. V430-01, V440-01; Invitrogen Corp. Publication, 1997.

Wang, C. et al., May 2006, "Refolding Recombinant Human Granulocyte Colony Stimulating Factor Expressed by *E. coli*: A Case Study Using the Unit of Simultaneous Renaturation and Purification of Proteins," BioProcess International, 48-53.

Scagnolari, C. et al., Dec. 2004, "Increased sensitivity of SARS-coronavirus to a combination of human type I and type II interferons," Antivir. Ther. 9(6): 1003-11.

Zeng, Zheng et al., Nov. 2000, "Transfer and expression of human interferon-α and its effect on HBV inhibition," Chinese Journal of Infectious Disease, 18(4):221-224.

Zheng, B. et al., Jul. 2004, "Potent inhibition of SARS-associated coronavirus (SCOV) infection and replication by type I interferons (IFN-alpha/beta) but not by type II interferon (IFN-gamma)," J. Interferon Cytokine Res., 24 (7):288-90.

Cao, Hongpeng, and Tao, Peizhen, 2001, "Effect of Anti-HBV of 6 Drugs Include Lamividine," Natl. Med. J. China, 81(16):1004-1007.

Fei et al., 1999, "Clinical Observation of Effect on Treatment of Chronic Hepatitis B by a Combination of Interferon α and Lamividine," Shandong Medical Journal, 39(11):3-4.

Gao et al., 1999, "Treatment of hepatitis virus related pediatric nephritis with IFN-α," Academic Journal of Jinlin Hospital, 12(1):24-26.

Lei et al., 1995, "Observation on Clinical Treatment of Chronic Hepatitis B by Purified Human Leucocyte Interferon-α," Chinese Journal of Practical Internal Medicine, 15(3):155-157.

Lang et al., 2002, "Observation on Serology and Histology of Patients with Chronic Hepatitis B after Interferon Treatment," Chin. J. Infect. Dis., 20(2):97-100.

Wang, Xiangye, and Li, Xuegang, 1994, "Comparing Effect of Three Drugs on Turning HBeAg to Negative," Qianwei Medical Journal, 11(4):197-198.

Chinese Patent No. CN 1062565C for Zhao, et al., Feb. 24, 1999, "Preparation, Method, and Application of Recombinant Human Consensus Interferon."

Alton, K. et al., 1983, "Production characterization and biological effects of recombinant DNA derived human IFN-α and IFN-γ analogs." In: De Maeger E, Schellekens H. eds. The Biology of Interferon System 2nd ed. Amsterdam: Elsevier Science Publishers, p. 119-128.

Blatt, L.M. et al., 1996, "The biological activity and molecular characterization of a novel synthetic interferon-alpha species, consensus interferon," Journal of Interferon and Cytokine Research, 16(7):489-499.

Heathcote, E.J.L. et al., 1998, "Re-treatment of chronic hepatitis C with consensus interferon," Hepatology 27(4):1136-1143.

Klein, M.L. et al., 1998, "Structural characterization of recombinant consensus interferon-alpha," Journal of Chromatography, 454:205-215.

Ozes, O.N. et al., 1992, "A comparison of interferon-con1 with natural recombinant interferons: antiviral, antiproliferative, and natural killer-inducing activities." J. Interferon Res., 12:55-59.

Pfeffer, L.M., 1997, "Biologic activity of natural and synthetic type 1 interferons," Seminars in Oncology, 24(3 suppl. 9):S9-63-S9-69.

Schleif, R.S., 1992, "DNA Looping," Ann. Rev. Biochem., 61:199-223.

Australian Examiner's Report for Sichuan Biotechnology Research Center, Australian Application No. 2003248419, Filed Sep. 26, 2003, Dated Dec. 12, 2005.

Australian Examiner's Report for Sichuan Biotechnology Research Center, Australian Application No. 2003248419, Filed Sep. 26, 2003, Dated Jun. 1, 2006.

Australian Notice of Acceptance for Sichuan Biotechnology Research Center, Australian Application No. 2003248419, Filed Sep. 26, 2003, Dated Dec. 18, 2006.

European Communication for Sichuan Biotechnology Research Center, European Application No. 02702211.0, Filed Sep. 25, 2003, Dated Dec. 14, 2006.

Indian Examination Report for Sichuan Biotechnology Research Center, Indian Application No. 279/MUM/2004, Filed Mar. 5, 2004, Dated Aug. 2, 2007.

Malaysian Examiner's Report for Sichuan Biotechnology Research Center, Malaysian Application No. PI 20033246, Filed Aug. 28, 2003, Dated Mar. 8, 2007.

Singapore Written Opinion for Huiyangtech (USA), Inc., Singapore Application No. 200601204-1, Filed Feb. 23, 2006, Dated Jul. 19, 2007.

Taiwanese Office Action for Sichuan Biotechnology Research Center, Taiwanese Application No. 92,123,846, Filed Aug. 28, 2003, Dated Sep. 21, 2006.

Taiwanese Formal Rejection for Sichuan Biotechnology Research Center, Taiwanese Application No. 92,123,846, filed Aug. 28, 2003, Dated Dec. 29, 2006.

Amato, Ivan, 2007, "Silent No Longer: Researchers Unearth Another Stratum of Meaning in the Genetic Code," Chemical and Engineering News, 85(4):38-40.

Cinatl et al., 2003, "Treatment of SARS with Human Interferons," The Lancet, 362:293-294.

Duan et al., 2003, "Anti-SARS virus activities of different recombinant human interferons in cell culture system," Chinese J. Clin. Virol., 17(3):205-208.

Higgins et al., 1983, "Intranasal Interferon as Protection Against Experimental Respiratory Coronavirus Infection in Volunteers," Antimicrobial Agents and Chemotherapy, 24(5):713-715.

Holland, C.C. and T.L. Wright, 1994, "New approaches to treatment of chronic viral hepatitis," Pathology (Phila.), 3(1).

Nackley, A.G. et al., 2006, "Human Catechol-O-Methyltransferase Haplotypes Modulate Protein Expression by Altering mRNA Secondary Structure," Science, 314:1930-1932.

Pyrc, K. et al., 2007, "Antiviral strategies against human coronaviruses," Infectious Disorders—Drug Targets, (7):59-66.

Zhao, Z. et al., 2003, "Description and clinical treatment of an early outbreak of Severe Acute Respiratory Syndrome (SARS) in Guangzhou, PR China," Journal of Med. Microbiol., 52:715-720.

Notice of Allowance and Fee(s) Due notice for Wei et al., U.S. Appl. No. 10/650,365, filed Aug. 28, 2003, dated Jul. 26, 2007.

U.S. Office Action for Wei et al., U.S. Appl. No. 10/650,365, filed Aug. 28, 2003, Dated Aug. 23, 2005.

U.S. Office Action for Wei et al., U.S. Appl. No. 10/650,365, filed Aug. 28, 2003, Dated Sep. 20, 2006.

U.S. Office Action for Wei et al., U.S. Appl. No. 10/650,365, filed Aug. 28, 2003, Dated Mar. 7, 2007.

U.S. Office Action for Guangwen Wei, U.S. Appl. No. 10/927,975, filed Aug. 26, 2004, Dated Apr. 3, 2007.

Advisory Action Before the Filing of an Appeal Brief for Guangwen Wei, U.S. Appl. No. 10/928,474, filed Aug. 26, 2004, Dated May 22, 2007.

U.S. Office Action for Guangwen Wei, U.S. Appl. No. 10/928,474, filed Aug. 26, 2004, Dated Aug. 9, 2007.

U.S. Office Action for Guangwen Wei, U.S. Appl. No. 10/928,474, filed Aug. 26, 2004, Dated Feb. 9, 2007.

U.S. Office Action for Guangwen Wei, U.S. Appl. No. 10/928,474, filed Aug. 26, 2004, Dated Aug. 22, 2006.

U.S. Office Action for Guangwen Wei, U.S. Appl. No. 11/077,813, filed Mar. 10, 2005, Dated Aug. 1, 2007.

U.S. Office Action for Guangwen Wei, U.S. Appl. No. 11/077,813, filed Mar. 10, 2005, Dated Nov. 27, 2006.

U.S. Office Action for Guangwen Wei, U.S. Appl. No. 11/077,813, filed Mar. 10, 2005, Dated Aug. 8, 2006.

U.S. Office Action for Wei et al., U.S. Appl. No. 10/650,365, filed Aug. 28, 2003, Dated Mar. 20, 2006.

U.S. Office Action for Guangwen Wei, U.S. Appl. No. 10/927,975, filed Aug. 26, 2004, Dated Sep. 19, 2007.

Notification of Transmittal of the International Search Report and the Written Opinion of the International Searching Authority (International Search Report and Written Opinion included), International Application No. PCT/IB2006/002340, Filed Mar. 9, 2006, Dated May 10, 2007.

International Search Report, Application No. PCT/US2004/028067 for Huiyangtech, Inc., "Uses of interferons with altered spatial structure," Filed Aug. 26, 2004, Dated Feb. 27, 2006, Date of Completion of the Search: Nov. 2, 2005.

International Search Report, Application No. PCT/CN02/00128 for Sichuan Biotechnology Research Center, "Recombination Super Compound Interferon Used as Hepatitis B Surface Antigen and E Antigen Inhibitor," Filed Feb. 28, 2002, Dated Aug. 8, 2002, Date of Completion of the Search: Jul. 23, 2002.

International Preliminary Examination Report, Application No. PCT/CN02/00128 for Sichuan Biotechnology Research Center, "Recombination Super Compound Interferon Used as Hepatitis B Surface Antigen and E Antigen Inhibitor," Filed Feb. 28, 2002, Dated Feb. 15, 2004.

Written Opinion of the International Searching Authority for PCT/US2004/028067, Dated Aug. 26, 2004 for Huiyangtech (USA) Inc., Dated Nov. 2, 2005.

Notification Concerning Transmittal of Copy of International Preliminary Report on Patentability (Chapter I of the Patent Cooperation Treaty) for PCT/IB2006/002340 for Guangwen WEI, Dated Sep. 20, 2007.

Written Opinion of the Australian Patent Office for SG 200601209-0, National Phase under Chapter II Based on PCT/US2004/028067 for Huiyangtech (USA) Inc., Dated Dec. 4, 2007.

Schulte-Frohlinde, et al., Feb. 21, 2002, "Different Activities of Type I interferons on Hepatitis B virus core promoter regulated transcription." Cytokine, 17(4): 214-220.

Yasuda, et al., 2000, "Spectrum of virus inhibition by consensus interferon YM643." Antiviral Chemistry & Chemotherapy, 11:337-341.

Wu, et al., 2003, "A hospital outbreak of severe acute respiratory syndrome in Guangzhou, China." Chinese Medicine Journal, 116(6):811-818.

Examiner's Report for WEI et al., European App'l No. 02702211.0, Filed Sep. 25, 2003, Dated Dec. 13, 2007.

Examiner's Written Opinion for Huiyangtech (USA), Inc., Singaporean App'l No. 200601209-0, Filed Feb. 23, 2006, Dated Jan. 8, 2008. (Australian Patent Office Written Opinion issued Dec. 4, 2007).

U.S. Office Action for Guangwen WEI, U.S. Appl. No. 10/928,474, Filed Aug. 26, 2004, Dated Jan. 4, 2008.

Advisory Action before the Filing of an Appeal Brief, U.S. Appl. No. 10/928,474, Filed Aug. 28, 2003, Dated Mar. 18, 2008.

Notice of Allowance for WEI et al., U.S. Appl. No. 10/650,365, Filed Aug. 28, 2003, Dated Dec. 12, 2007.

U.S. Office Action for Guangwen WEI, U.S. Appl. No. 11/077,813, Filed Mar. 10, 2005, Dated Feb. 6, 2008.

U.S. Office Action for Guangwen WEI, U.S. Appl. No. 10/927,975, Filed Aug. 26, 2004, Dated Apr. 2, 2008.

* cited by examiner

Figure 1

```
     5'         11          21          31          41          51
  +1 M C D L P Q T H S L G N R R A L I L L A
     1  ATGTGCGACC  TGCCGCAGAC  CCACTCCCTG  GGTAACCGTC  GTGCTCTGAT
CCTGCTGGCT
        TACACGCTGG  ACGGCGTCTG  GGTGAGGGAC  CCATTGGCAG  CACGAGACTA
GGACGACCGA

5'         71          81          91         101         111
  +1 Q M R R I S P F S C L K D R H D F G F P
    61  CAGATGCGTC  GTATCTCCCC  GTTCTCCTGC  CTGAAAGACC  GTCACGACTT
CGGTTTCCCG
        GTCTACGCAG  CATAGAGGGG  CAAGAGGACG  GACTTTCTGG  CAGTGCTGAA
GCCAAAGGGC

5'        131         141         151         161         171
  +1 Q E E F D G N Q F Q K A Q A I S V L H E
   121  CAGGAAGAAT  TCGACGGTAA  CCAGTTCCAG  AAAGCTCAGG  CTATCTCCGT
TCTGCACGAA
        GTCCTTCTTA  AGCTGCCATT  GGTCAAGGTC  TTTCGAGTCC  GATAGAGGCA
AGACGTGCTT

5'        191         201         211         221         231
  +1 M I Q Q T F N L F S T K D S S A A W D E
   181  ATGATCCAGC  AGACCTTCAA  CCTGTTCTCC  ACCAAAGACT  CCTCCGCTGC
TTGGGACGAA
        TACTAGGTCG  TCTGGAAGTT  GGACAAGAGG  TGGTTTCTGA  GGAGGCGACG
AACCCTGCTT

5'        251         261         271         281         291
  +1 S L L E K F Y T E L Y Q Q L N D L E A C
   241  TCCCTGCTGG  AAAAATTCTA  CACCGAACTG  TACCAGCAGC  TGAACGACCT
GGAAGCTTGC
        AGGGACGACC  TTTTTAAGAT  GTGGCTTGAC  ATGGTCGTCG  ACTTGCTGGA
CCTTCGAACG

5'        311         321         331         341         351
  +1 V I Q E V G V E E T P L M N V D S I L A
   301  GTTATCCAGG  AAGTTGGTGT  TGAAGAAACC  CCGCTGATGA  ACGTTGACTC
CATCCTGGCT
        CAATAGGTCC  TTCAACCACA  ACTTCTTTGG  GGCGACTACT  TGCAACTGAG
GTAGGACCGA

5'        371         381         391         401         411
  +1 V K K Y F Q R I T L Y L T E K K Y S P C
   361  GTTAAAAAAT  ACTTCCAGCG  TATCACCCTG  TACCTGACCG  AAAAAAAATA
CTCCCCGTGC
        CAATTTTTTA  TGAAGGTCGC  ATAGTGGGAC  ATGGACTGGC  TTTTTTTTAT
GAGGGGCACG

5'        431         441         451         461         471
  +1 A W E V V R A E I M R S F S L S T N L Q
   421  GCTTGGGAAG  TTGTTCGTGC  TGAAATCATG  CGTTCCTTCT  CCCTGTCCAC
CAACCTGCAG
        CGAACCCTTC  AACAAGCACG  ACTTTAGTAC  GCAAGGAAGA  GGGACAGGTG
GTTGGACGTC

5'        491         501
  +1 E R L R R K E #
   481  GAACGTCTGC  GTCGTAAAGA  ATAA
        CTTGCAGACG  CAGCATTTCT  TATT
```

Figure 2

```
5'          11          21          31          41          51
+1  M C D   L P Q T   H S L   G N R   R A L I   L L A
 1  ATGTGTGATT TACCTCAAAC TCATTCTCTT GGTAACCGTC GCGCTCTGAT TCTGCTGGCA
    TACACACTAA ATGGAGTTTG AGTAAGAGAA CCATTGGCAG CGCGAGACTA AGACGACCGT

5'          71          81          91          1           11
+1  Q M R   R I S P   F S C   L K D   R H D F   G F P
61  CAGATGCGTC GTATTTCCCC GTTTAGCTGC CTGAAAGACC GTCACGACTT CGGCTTTCCG
    GTCTACGCAG CATAAAGGGG CAAATCGACG GACTTTCTGG CAGTGCTGAA GCCGAAAGGC

5'          31          41          51          61          71
+1  Q E E   F D G N   Q F Q   K A Q   A I S V   L H E
121 CAAGAAGAGT TCGATGGCAA CCAATTCCAG AAAGCTCAGG CAATCTCTGT ACTGCACGAA
    GTTCTTCTCA AGCTACCGTT GGTTAAGGTC TTTCGAGTCC GTTAGAGACA TGACGTGCTT

5'          91          1           11          21          31
+1  M I Q   Q T F N   L F S   T K D   S S A A   W D E
181 ATGATCCAAC AGACCTTCAA CCTGTTTTCC ACTAAAGACA GCTCTGCTGC TTGGGACGAA
    TACTAGGTTG TCTGGAAGTT GGACAAAAGG TGATTTCTGT CGAGACGACG AACCCTGCTT

5'          51          61          71          81          91
+1  S L L   E K F Y   T E L   Y Q Q   L N D L   E A C
241 AGCTTGCTGG AGAAGTTCTA CACTGAACTG TATCAGCAGC TGAACGACCT GGAAGCATGC
    TCGAACGACC TCTTCAAGAT GTGACTTGAC ATAGTCGTCG ACTTGCTGGA CCTTCGTACG

5'          11          21          31          41          51
+1  V I Q   E V G V   E E T   P L M   N V D S   I L A
301 GTAATCCAGG AAGTTGGTGT AGAAGAGACT CCGCTGATGA ACGTCGACTC TATTCTGGCA
    CATTAGGTCC TTCAACCACA TCTTCTCTGA GGCGACTACT TGCAGCTGAG ATAAGACCGT
```

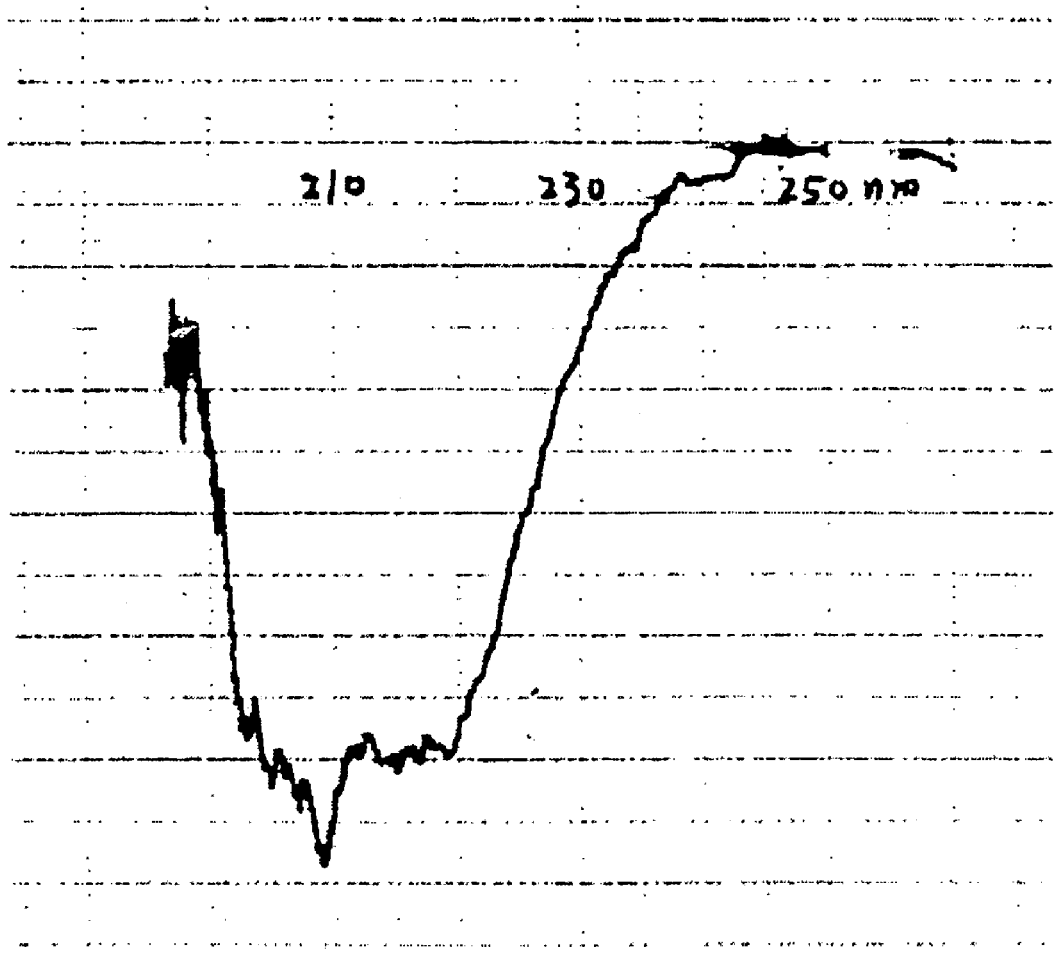
Figure 6-A

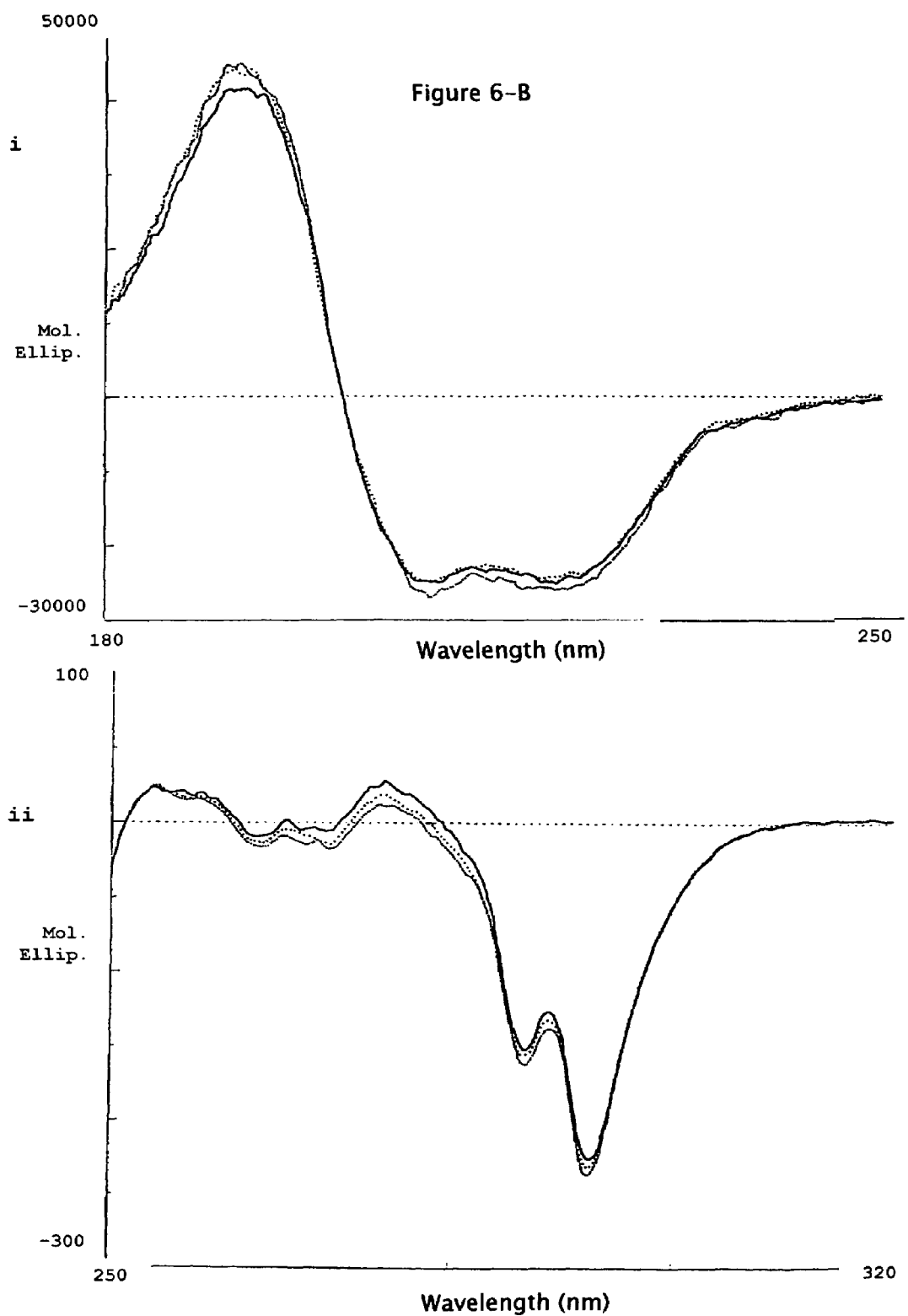
Figure 6-B

Figure 6-C
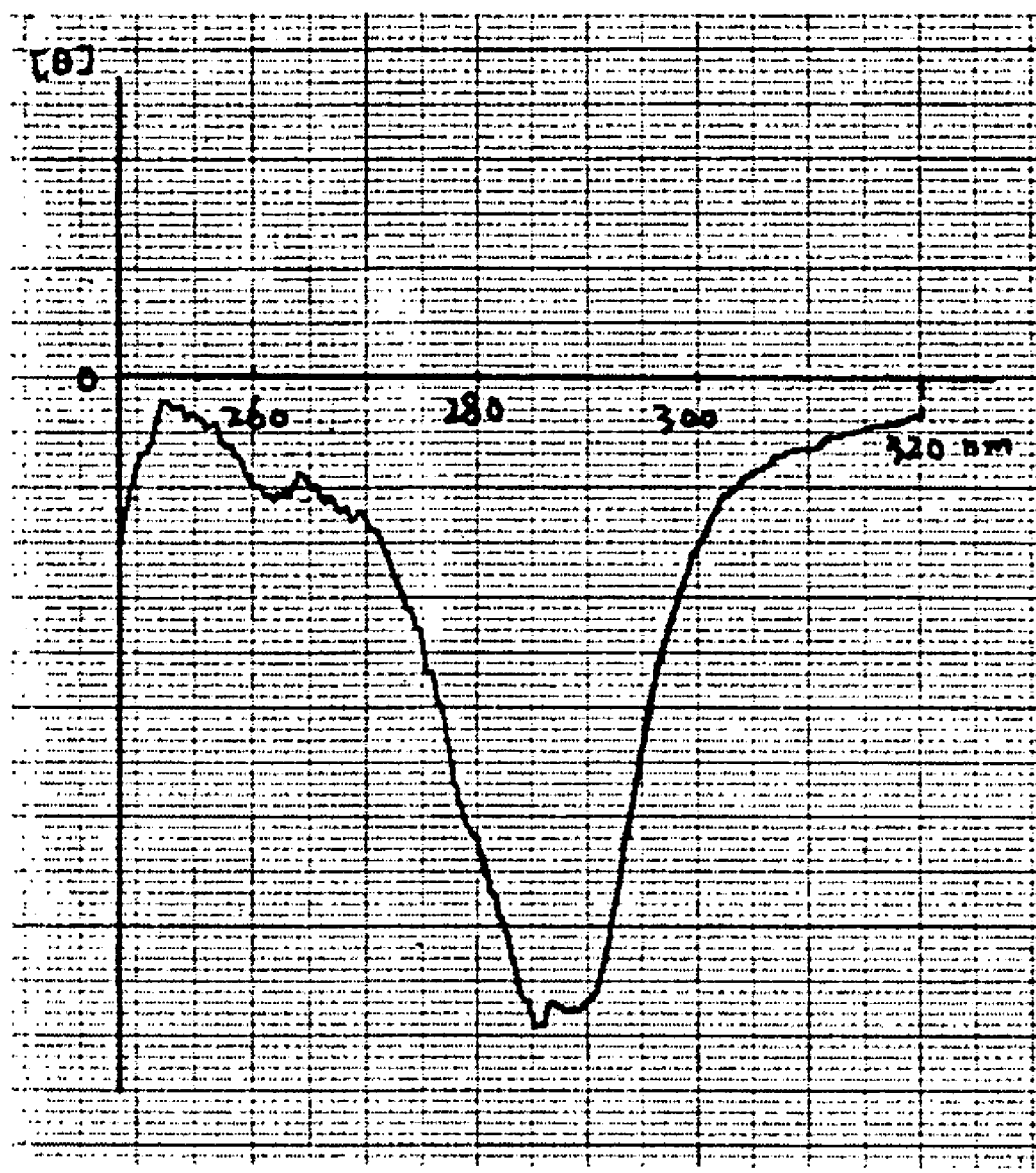

Figure 6-D
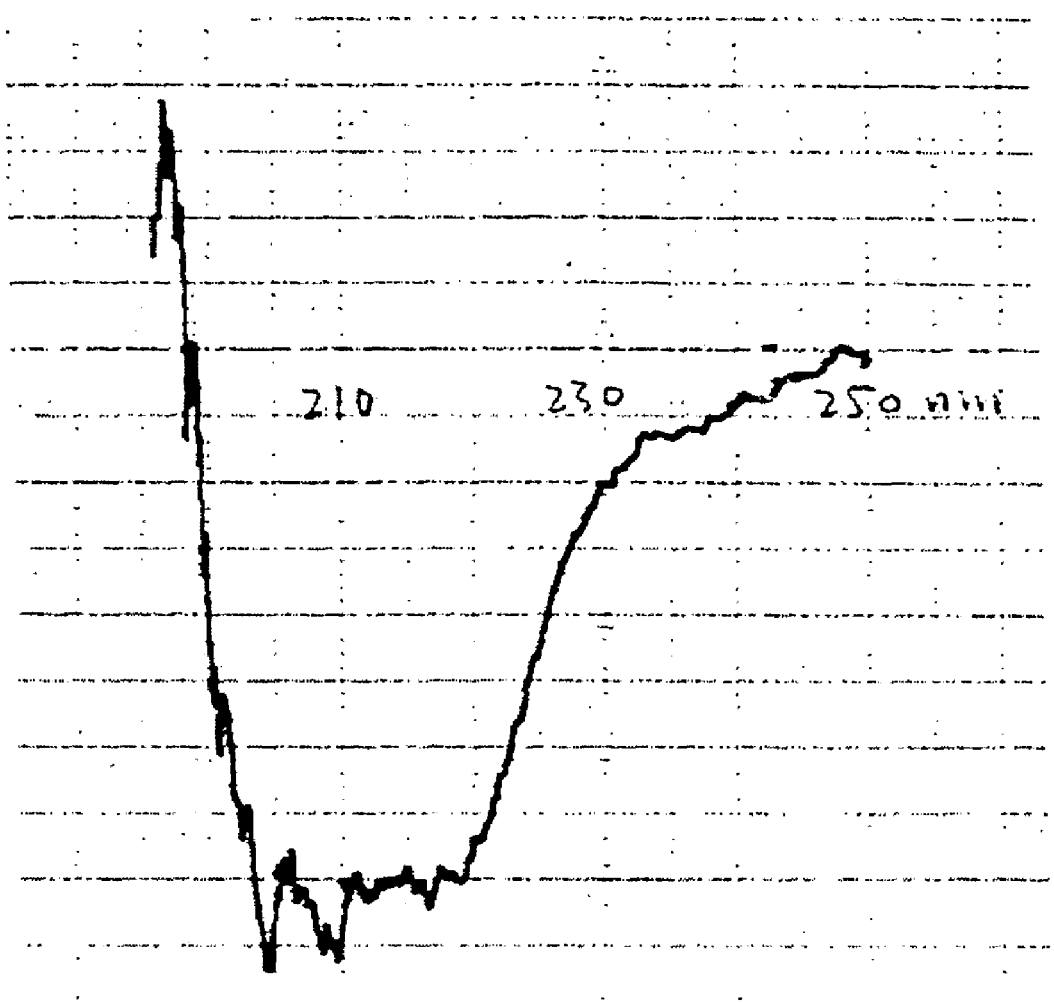

SEQUENCE LISTING

<160> NUMBER OF SEQ ID NOS: 13

<210> SEQ ID NO 1
<211> LENGTH: 504
<212> TYPE: DNA
<213> ORGANISM: Artificial
<220> FEATURE:
<223> OTHER INFORMATION: chemically synthesized
<220> FEATURE:
<221> NAME/KEY: CDS
<222> LOCATION: (1)..(504)

<400> SEQUENCE: 1

```
atg tgc gac ctg ccg cag acc cac tcc ctg ggt aac cgt cgt gct ctg      48
Met Cys Asp Leu Pro Gln Thr His Ser Leu Gly Asn Arg Arg Ala Leu
1               5                   10                  15 atc ctg ctg gct cag atg cgt cgt atc tcc ccg ttc tcc tgc ctg aaa      96
Ile Leu Leu Ala Gln Met Arg Arg Ile Ser Pro Phe Ser Cys Leu Lys
                20                  25                  30 gac cgt cac gac ttc ggt ttc ccg cag gaa gaa ttc gac ggt aac cag     144
Asp Arg His Asp Phe Gly Phe Pro Gln Glu Glu Phe Asp Gly Asn Gln
            35                  40                  45 ttc cag aaa gct cag gct atc tcc gtt ctg cac gaa atg atc cag cag     192
Phe Gln Lys Ala Gln Ala Ile Ser Val Leu His Glu Met Ile Gln Gln
        50                  55                  60 acc ttc aac ctg ttc tcc acc aaa gac tcc tcc gct gct tgg gac gaa     240
Thr Phe Asn Leu Phe Ser Thr Lys Asp Ser Ser Ala Ala Trp Asp Glu
65                  70                  75                  80 tcc ctg ctg gaa aaa ttc tac acc gaa ctg tac cag cag ctg aac gac     288
Ser Leu Leu Glu Lys Phe Tyr Thr Glu Leu Tyr Gln Gln Leu Asn Asp
                85                  90                  95 ctg gaa gct tgc gtt atc cag gaa gtt ggt gtt gaa gaa acc ccg ctg     336
Leu Glu Ala Cys Val Ile Gln Glu Val Gly Val Glu Glu Thr Pro Leu
            100                 105                 110 atg aac gtt gac tcc atc ctg gct gtt aaa aaa tac ttc cag cgt atc     384
Met Asn Val Asp Ser Ile Leu Ala Val Lys Lys Tyr Phe Gln Arg Ile
        115                 120                 125 acc ctg tac ctg acc gaa aaa aaa tac tcc ccg tgc gct tgg gaa gtt     432
Thr Leu Tyr Leu Thr Glu Lys Lys Tyr Ser Pro Cys Ala Trp Glu Val
    130                 135                 140 gtt cgt gct gaa atc atg cgt tcc ttc tcc ctg tcc acc aac ctg cag     480
Val Arg Ala Glu Ile Met Arg Ser Phe Ser Leu Ser Thr Asn Leu Gln
145                 150                 155                 160 gaa cgt ctg cgt cgt aaa gaa taa                                     504
Glu Arg Leu Arg Arg Lys Glu
                165
```

<210> SEQ ID NO 2
<211> LENGTH: 167
<212> TYPE: PRT
<213> ORGANISM: Artificial
<220> FEATURE:
<223> OTHER INFORMATION: Synthetic Construct

<400> SEQUENCE: 2

```
Met Cys Asp Leu Pro Gln Thr His Ser Leu Gly Asn Arg Arg Ala Leu
1               5                   10                  15

Ile Leu Leu Ala Gln Met Arg Arg Ile Ser Pro Phe Ser Cys Leu Lys
                20                  25                  30

Asp Arg His Asp Phe Gly Phe Pro Gln Glu Glu Phe Asp Gly Asn Gln
            35                  40                  45
```

```
Phe Gln Lys Ala Gln Ala Ile Ser Val Leu His Glu Met Ile Gln Gln
 50                  55                  60
Thr Phe Asn Leu Phe Ser Thr Lys Asp Ser Ser Ala Ala Trp Asp Glu
 65                  70                  75                  80
Ser Leu Leu Glu Lys Phe Tyr Thr Glu Leu Tyr Gln Gln Leu Asn Asp
                 85                  90                  95
Leu Glu Ala Cys Val Ile Gln Glu Val Gly Val Glu Thr Pro Leu
            100                 105                 110
Met Asn Val Asp Ser Ile Leu Ala Val Lys Lys Tyr Phe Gln Arg Ile
        115                 120                 125
Thr Leu Tyr Leu Thr Glu Lys Lys Tyr Ser Pro Cys Ala Trp Glu Val
    130                 135                 140
Val Arg Ala Glu Ile Met Arg Ser Phe Ser Leu Ser Thr Asn Leu Gln
145                 150                 155                 160
Glu Arg Leu Arg Arg Lys Glu
                165
```

<210> SEQ ID NO 3  
<211> LENGTH: 360  
<212> TYPE: DNA  
<213> ORGANISM: Artificial  
<220> FEATURE:  
<223> OTHER INFORMATION: chemically synthesized  
<220> FEATURE:  
<221> NAME/KEY: CDS  
<222> LOCATION: (1)..(360)

<400> SEQUENCE: 3

```
atg tgt gat tta cct caa act cat tct ctt ggt aac cgt cgc gct ctg      48
Met Cys Asp Leu Pro Gln Thr His Ser Leu Gly Asn Arg Arg Ala Leu
 1               5                  10                  15 att ctg ctg gca cag atg cgt cgt att tcc ccg ttt agc tgc ctg aaa      96
Ile Leu Leu Ala Gln Met Arg Arg Ile Ser Pro Phe Ser Cys Leu Lys
                20                  25                  30 gac cgt cac gac ttc ggc ttt ccg caa gaa gag ttc gat ggc aac caa     144
Asp Arg His Asp Phe Gly Phe Pro Gln Glu Glu Phe Asp Gly Asn Gln
            35                  40                  45 ttc cag aaa gct cag gca atc tct gta ctg cac gaa atg atc caa cag     192
Phe Gln Lys Ala Gln Ala Ile Ser Val Leu His Glu Met Ile Gln Gln
 50                  55                  60 acc ttc aac ctg ttt tcc act aaa gac agc tct gct gct tgg gac gaa     240
Thr Phe Asn Leu Phe Ser Thr Lys Asp Ser Ser Ala Ala Trp Asp Glu
 65                  70                  75                  80 agc ttg ctg gag aag ttc tac act gaa ctg tat cag cag ctg aac gac     288
Ser Leu Leu Glu Lys Phe Tyr Thr Glu Leu Tyr Gln Gln Leu Asn Asp
                 85                  90                  95 ctg gaa gca tgc gta atc cag gaa gtt ggt gta gaa gag act ccg ctg     336
Leu Glu Ala Cys Val Ile Gln Glu Val Gly Val Glu Glu Thr Pro Leu
            100                 105                 110 atg aac gtc gac tct att ctg gca                                     360
Met Asn Val Asp Ser Ile Leu Ala
        115                 120
```

<210> SEQ ID NO 4  
<211> LENGTH: 120  
<212> TYPE: PRT  
<213> ORGANISM: Artificial  
<220> FEATURE:  
<223> OTHER INFORMATION: Synthetic Construct

<400> SEQUENCE: 4

```
Met Cys Asp Leu Pro Gln Thr His Ser Leu Gly Asn Arg Arg Ala Leu
1               5                   10                  15

Ile Leu Leu Ala Gln Met Arg Arg Ile Ser Pro Phe Ser Cys Leu Lys
            20                  25                  30

Asp Arg His Asp Phe Gly Phe Pro Gln Glu Glu Phe Asp Gly Asn Gln
            35                  40                  45

Phe Gln Lys Ala Gln Ala Ile Ser Val Leu His Glu Met Ile Gln Gln
        50                  55                  60

Thr Phe Asn Leu Phe Ser Thr Lys Asp Ser Ser Ala Ala Trp Asp Glu
65                  70                  75                  80

Ser Leu Leu Glu Lys Phe Tyr Thr Glu Leu Tyr Gln Gln Leu Asn Asp
                85                  90                  95

Leu Glu Ala Cys Val Ile Gln Glu Val Gly Val Glu Glu Thr Pro Leu
            100                 105                 110

Met Asn Val Asp Ser Ile Leu Ala
        115                 120

<210> SEQ ID NO 5
<211> LENGTH: 108
<212> TYPE: DNA
<213> ORGANISM: Artificial
<220> FEATURE:
<223> OTHER INFORMATION: chemically synthesized
<220> FEATURE:
<221> NAME/KEY: CDS
<222> LOCATION: (1)..(108)

<400> SEQUENCE: 5 atg tgc gac ctg ccg cag acc cac tcc ctg ggt aac cgt cgt gct ctg      48
Met Cys Asp Leu Pro Gln Thr His Ser Leu Gly Asn Arg Arg Ala Leu
1               5                   10                  15 atc ctg ctg gct cag atg cgt cgt atc tcc ccg ttc tcc tgc ctg aaa      96
Ile Leu Leu Ala Gln Met Arg Arg Ile Ser Pro Phe Ser Cys Leu Lys
            20                  25                  30 gac cgt cac gac                                                     108
Asp Arg His Asp
            35

<210> SEQ ID NO 6
<211> LENGTH: 36
<212> TYPE: PRT
<213> ORGANISM: Artificial
<220> FEATURE:
<223> OTHER INFORMATION: Synthetic Construct

<400> SEQUENCE: 6

Met Cys Asp Leu Pro Gln Thr His Ser Leu Gly Asn Arg Arg Ala Leu
1               5                   10                  15

Ile Leu Leu Ala Gln Met Arg Arg Ile Ser Pro Phe Ser Cys Leu Lys
            20                  25                  30

Asp Arg His Asp
            35

<210> SEQ ID NO 7
<211> LENGTH: 107
<212> TYPE: DNA
<213> ORGANISM: Artificial
<220> FEATURE:
<223> OTHER INFORMATION: chemically synthesized
<220> FEATURE:
<221> NAME/KEY: Unsure
<222> LOCATION: (1)..(107)
```

-continued

<400> SEQUENCE: 7
ctgaaagacc gtcacgactt cggtttcccg caggagaggt tcgacggtaa ccagttccag    60
aagctcaggc tatctccgtt ctgcacgaaa tgatccagca gaccttc                 107

<210> SEQ ID NO 8
<211> LENGTH: 103
<212> TYPE: DNA
<213> ORGANISM: Artificial
<220> FEATURE:
<223> OTHER INFORMATION: chemically synthesized
<220> FEATURE:
<221> NAME/KEY: Unsure
<222> LOCATION: (1)..(103)

<400> SEQUENCE: 8
gctgctggta cagttcggtg tagaattttt ccagcaggga ttcgtcccaa gcagcggagg    60
agtctttggt ggagaacagg ttgaaggtct gctggatcat ttc                    103

<210> SEQ ID NO 9
<211> LENGTH: 103
<212> TYPE: DNA
<213> ORGANISM: Artificial
<220> FEATURE:
<223> OTHER INFORMATION: chemically synthesized
<220> FEATURE:
<221> NAME/KEY: Unsure
<222> LOCATION: (1)..(103)

<400> SEQUENCE: 9
atccctgctg gaaaaattct acaccgaact gtaccagcag ctgaacgacc tggaagcttg    60
cgttatccag gaagttggtg ttgaagaaac cccgctgatg aac                    103

<210> SEQ ID NO 10
<211> LENGTH: 106
<212> TYPE: DNA
<213> ORGANISM: Artificial
<220> FEATURE:
<223> OTHER INFORMATION: chemically synthesized
<220> FEATURE:
<221> NAME/KEY: Unsure
<222> LOCATION: (1)..(106)

<400> SEQUENCE: 10
gaagaaaccc cgctgatgaa cgttgactcc atcctggctg ttaaaaaata cttccagcgt    60
atcaccctgt acctgaccga aaaaaatac tccccgtgcg cttggg                 106

<210> SEQ ID NO 11
<211> LENGTH: 112
<212> TYPE: DNA
<213> ORGANISM: Artificial
<220> FEATURE:
<223> OTHER INFORMATION: chemically synthesized
<220> FEATURE:
<221> NAME/KEY: Unsure
<222> LOCATION: (1)..(112)

<400> SEQUENCE: 11
ttattcttta cgacgcagac gttcctgcag gttggtggac agggagaagg aacgcatgat    60
ttcagcacga acaacttccc aagcgcacgg ggagtatttt ttttcggtca gg          112

<210> SEQ ID NO 12
<211> LENGTH: 31
<212> TYPE: DNA

```
<213> ORGANISM: Artificial
<220> FEATURE:
<223> OTHER INFORMATION: chemically synthesized
<220> FEATURE:
<221> NAME/KEY: Unsure
<222> LOCATION: (1)..(31)

<400> SEQUENCE: 12
atcggccata tgtgcgacct gccgcagacc c                                          31

<210> SEQ ID NO 13
<211> LENGTH: 40
<212> TYPE: DNA
<213> ORGANISM: Artificial
<220> FEATURE:
<223> OTHER INFORMATION: chemically synthesized
<220> FEATURE:
<221> NAME/KEY: Unsure
<222> LOCATION: (1)..(40)

<400> SEQUENCE: 13
actgccaggc tgcagttatt ctttacgacg cagacgttcc                                 40
```

NUCLEIC ACID ENCODING RECOMBINANT INTERFERON

The application disclosed herein claims benefit of U.S. Ser. No. 60/498,449, Filed Aug. 28, 2003. This application claims priority of Indian Application No. 279/MUM/2004, filed Mar. 5, 2004, and Indian Application No. 280/MUM/2004, filed Mar. 5, 2004. The contents of the preceding applications are hereby incorporated in their entireties by reference into this application.

Throughout this application, various publications are referenced. Disclosures of these publications in their entireties are hereby incorporated by reference into this application in order to more fully describe the state of the art to which this invention pertains.

FIELD OF THE INVENTION

This invention is related to a recombinant super-compound interferon (rSIFN-co) with changed spatial configuration. One characteristic of rSIFN-co in this invention is that it inhibits DNA (deoxyribonucleic acid) duplication of the hepatitis B virus as well as the secretion of HBsAg and HBeAg.

BACKGROUND OF THE INVENTION

IFN-con is a new interferon molecule constructed with the most popular conservative amino acid found in natural human α-IFN subtypes using genetic engineering methods. U.S. Pat. Nos. 4,695,623 and 4,897,471 have described it. IFN-con had been proved to have broad-spectrum IFN activity and virus- and tumor-inhibition and natural killer cell activity. U.S. Pat. No. 5,372,808 by Amgen, Inc. addresses treatment IFN-con. Chinese Patent No. 97193506.8 by Amgen, Inc. addresses re-treatment of consensus interferon on hepatitis C. Chinese Patent No. 98114663.5 by Shenzhen Jiusheng Bio-engineering Ltd. addresses recombinant human consensus interferon-α treatment for hepatitis B and hepatitis C.

The United States Food and Drug Administration (FDA) authorized Amgen, Inc. to produce INFERGEN® (interferon alfacon-1) with *E. Coli.* for clinical hepatitis C treatment at the end of 1997.

Hepatitis B patients can be identified when detecting HBsAg and HBeAg. α-IFN is commonly used in clinics to treat hepatitis B. IFN binds superficial cell membrane receptors, inhibiting DNA and RNA (ribonucleic acid) duplication, including inducing some enzymes to prevent duplication of the virus in hepatitis-infected cells. All IFNs can inhibit only the DNA duplication of viruses, not the e and s antigen.

This disclosure describes recombinant super-compound interferon, method to produce the same, and uses thereof.

SUMMARY OF THE INVENTION

This invention provides a recombinant super-compound interferon or an equivalent thereof with changed spatial configuration. An equivalent is a molecule which is similar in function to the super-compound interferon. The super-compound interferon possesses anti-viral or anti-tumor activity. This invention also provides artificial gene which codes for the super-compound interferon or its equivalent.

This invention provides a process for production of recombinant super-compound interferon comprising introducing an artificial gene with selected codon preference into an appropriate host, culturing said introduced host in an appropriate condition permitting expression of said super-compound interferon, and harvesting the expressed super-compound interferon.

This invention provides a composition comprising the recombinant super-compound interferon or its equivalent and a suitable carrier. This invention further provides a pharmaceutical composition comprising the recombinant super-compound interferon or its equivalent and a pharmaceutically acceptable carrier.

This invention provides a method for treating viral diseases or tumor in a subject comprising administering to the subject an effective amount of the super-compound interferon or its equivalent.

This invention provides the above-described method wherein super-compound interferon was administered orally, via vein injection, muscle injection, peritoneal injection, subcutaneous injection, nasal or mucosal administration, or by inhalation via an inspirator.

DETAILED DESCRIPTION OF THE FIGURES

Figures 1, 8A:
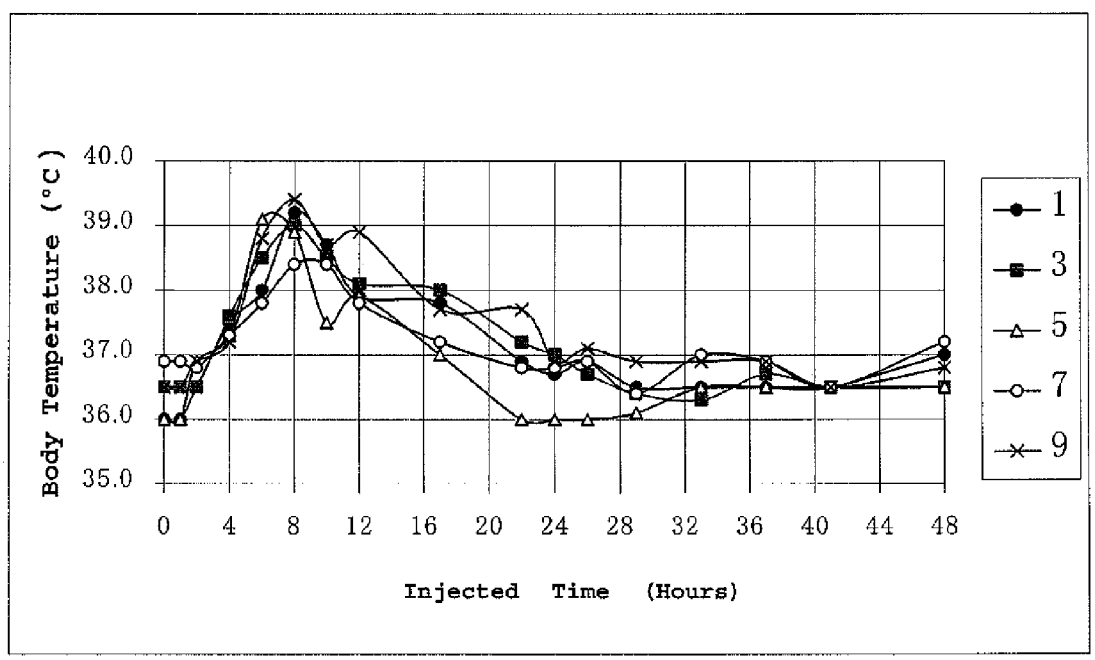

FIG. 1. rSIFN-co cDNA sequence (SEQ ID NOs:1 and 5) designed according to *E. Coil.* codon usage and deduced rSIFN-co amino acid sequence (SEQ ID NO:2)

Figures 2, 8A:
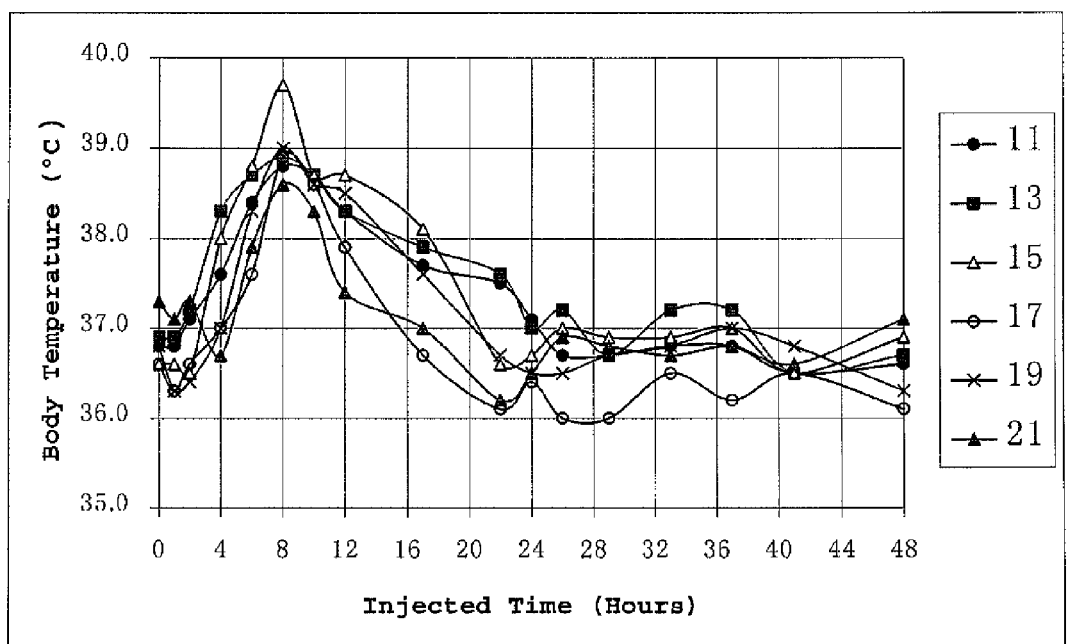

FIG. 2. Sequence of another super-compound interferon cDNA sequence (SEQ ID NOs:3 and 6) designed according to *E. Coli.* codon usage and deduced rSIFN-co amino acid sequence (SEQ ID NO:4).

FIG. 3. Diagram of pLac T7 cloning vector plasmid

Figure 4:
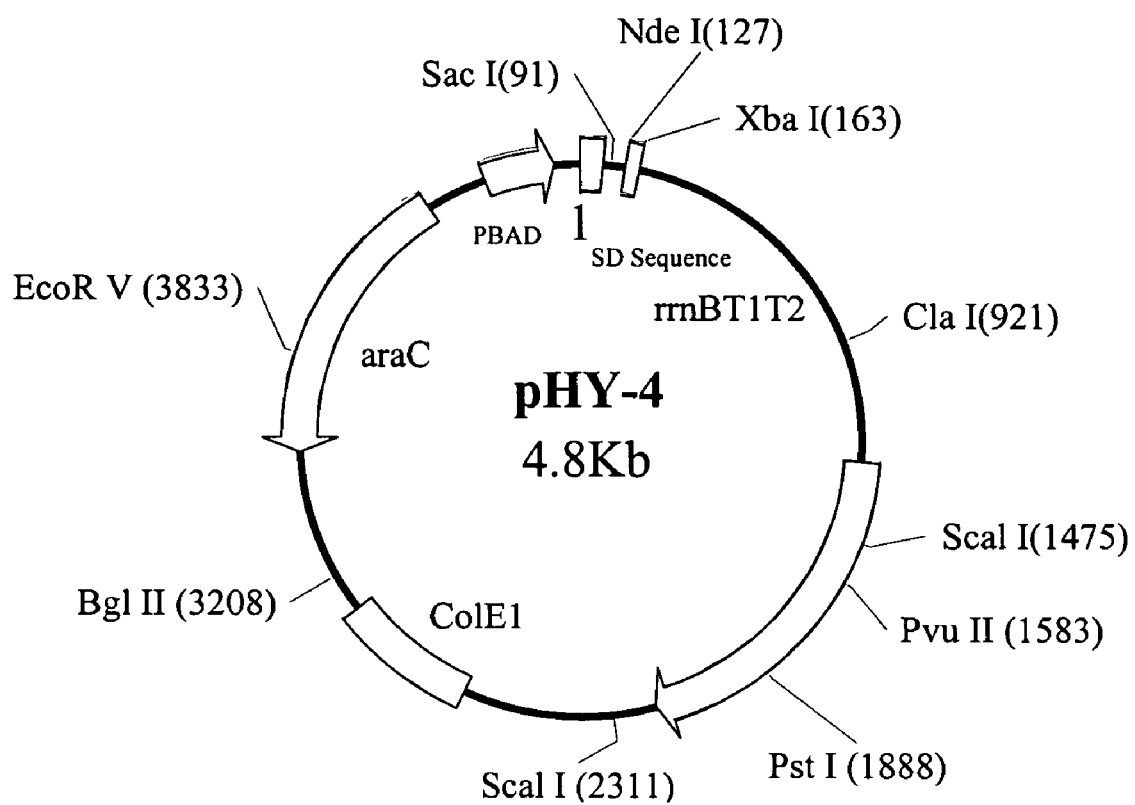

FIG. 4. Diagram of pHY-4 expression vector plasmid

Figure 5:
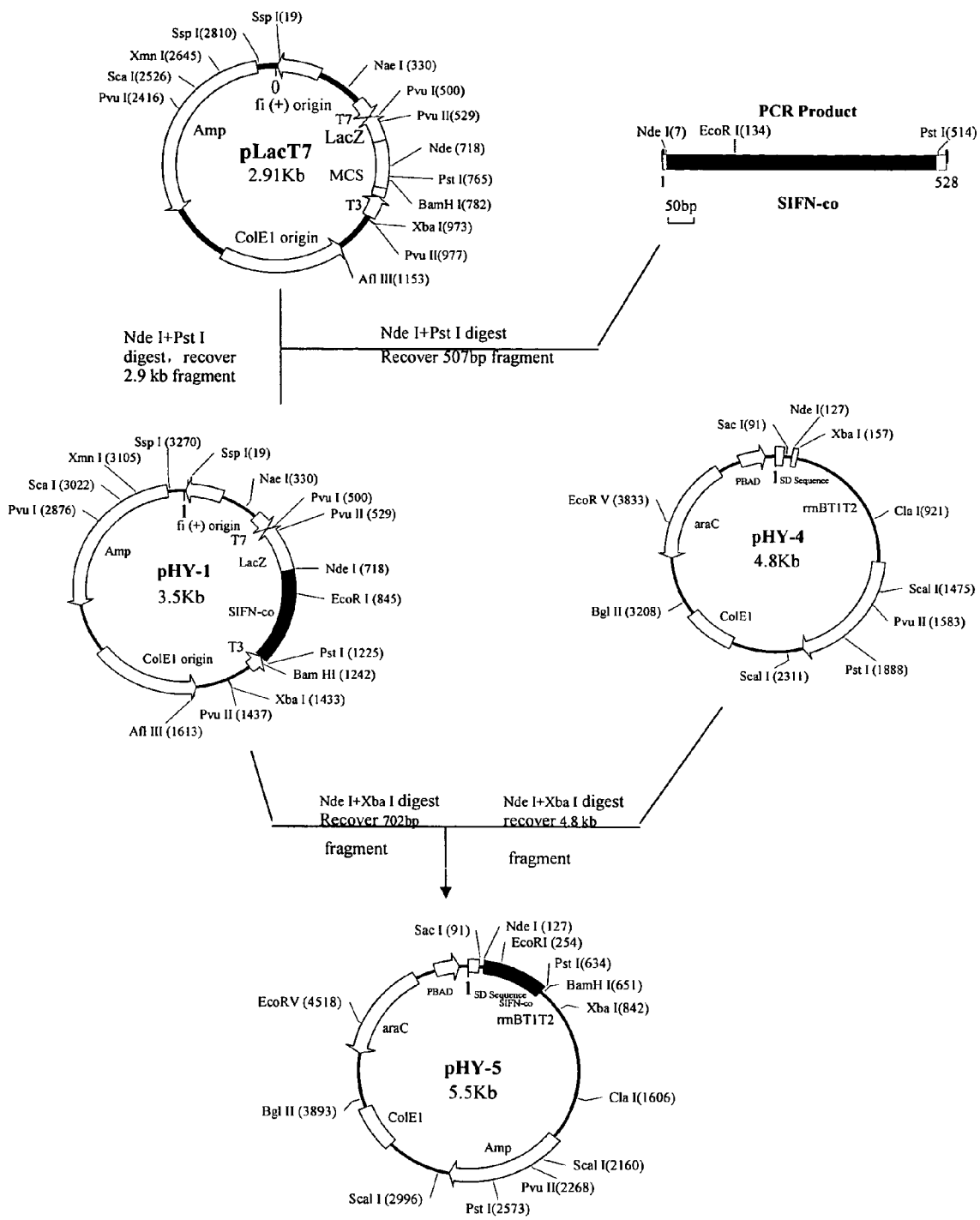

FIG. 5. Construction process of expression plasmid pHY-5

FIG. 6-A. Circular Dichroism spectrum of INFERGEN® (interferon alfacon-1)

Spectrum range: 250 nm-190 nm

Sensitivity: 2 m°/ cm

Light path: 0.20 cm

Equipment: Circular Dichroism J-500C

Samples: contains 30 μg/ml IFN-con1, 5.9 mg/ml of NaCl and 3.8 mg/ml of $Na_2PO_4$, pH 7.0.

INFERGEN® (interferon alfacon-1), made by Amgen Inc., also known as consensus interferon, is marketed for the treatment of adults with chronic hepatitis C virus (HCV) infections. It is currently the only FDA approved, bio-optimized interferon developed through rational drug design and the only interferon with data in the label specifically for non-responding or refractory patients. InterMune's sales force re-launched INFERGEN® in January 2002 with an active campaign to educate U.S. hepatologists about the safe and appropriate use of INFERGEN®, which represents new hope for the more than 50 percent of HCV patients who fail other currently available therapies.

FIG. 6-B. Circular Dichroism spectrum of INFERGEN® From Reference [Journal of Interferon and Cytokine Research. 16:489-499 (1996)]

Circular dichroism spectra of concensus interferon subforms. Concensus interferon was fractionated using an anion exchange column. Samples were dialyzed into 10 mM sodium phosphate, pH 7.4. Measurements were made on Jasco J-170 spectopolarimeter, in a cell thermostat at 15° C. (——), acylated form; (—) cis terminal form; (•••), met terminal form. A. Far UV Spectrum. B. Near UV Spectrum.

FIG. 6-C. Circular Dichroism spectrum of rSIFN-co

Spectrum range: 320 nm-250 nm

Sensitivity: 2 m°/cm

Light path: 2 cm

Equipment: Circular Dichroism J-500C

Samples: contains 0.5 mg/ml rSIFN-co, 5.9 mg/ml of NaCl and 3.8 mg/ml of $Na_2PO_4$, pH 7.0.

FIG. 6-D. Circular Dichroism spectrum of rSIFN-co

Spectrum range: 250 nm-190 nm
Sensitivity: 2 m°/cm
Light path: 0.20 cm
Equipment: Circular Dichroism J-500C
Samples: contains 30 μg/ml rSIFN-co, 5.9 mg/ml of NaCl and 3.8 mg/ml of $Na_2PO_4$, pH 7.0.

Clearly, as evidenced by the above spectra, the secondary or even tertiary structure of rSTFN-co is different from INFERGEN® (interferon alfacon-1).

Figure 7:
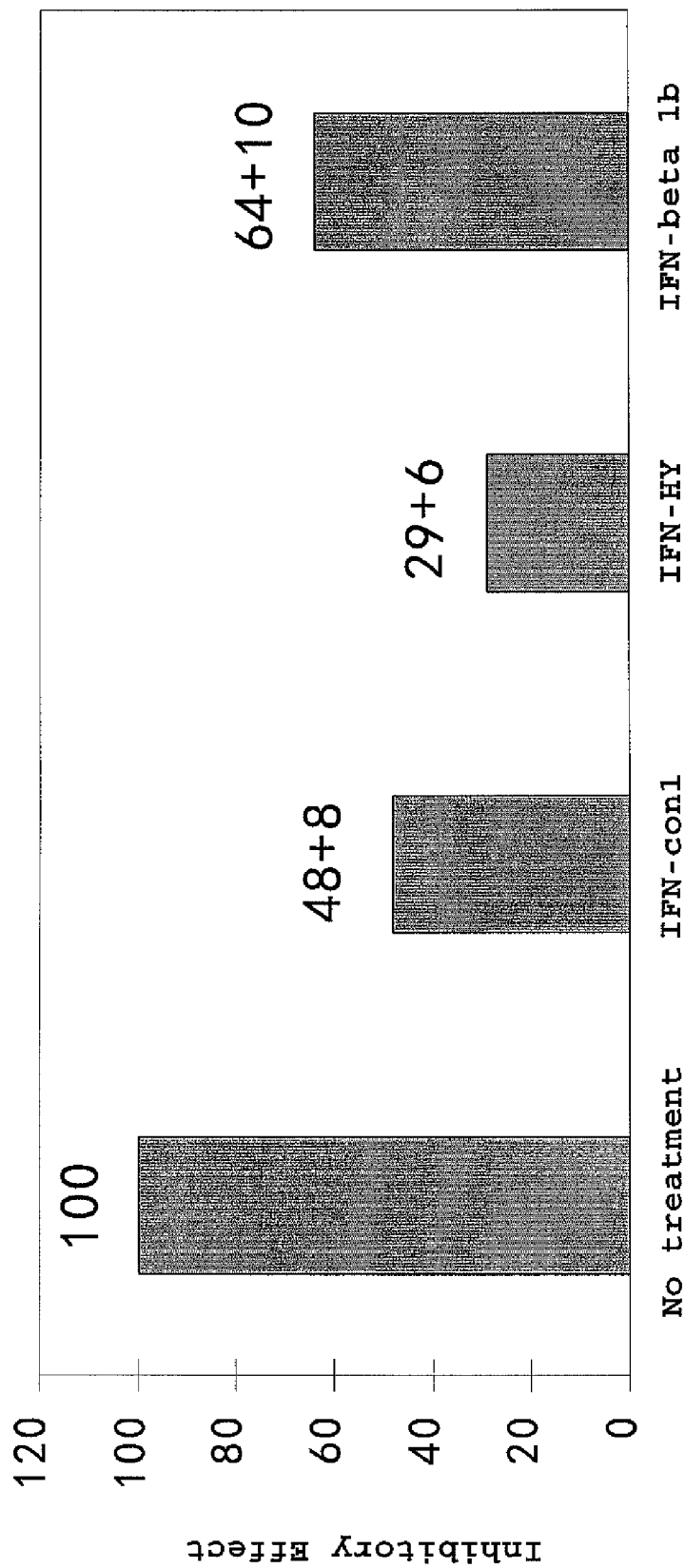

FIG. 7. Comparison of Inhibition Effects of Different Interferons on HBV Gene Expression FIG. 8A-1. Curves of Changes of Body Temperature in Group A (5 patients)

This figure is the record of body temperature changes of 5 patients in Group A.

FIG. 8A-2. Curves of Changes of Body Temperature in Group A (6 patients)

This figure is the record of body temperature changes of the other 6 patients in Group A.

Figures 1, 8B:
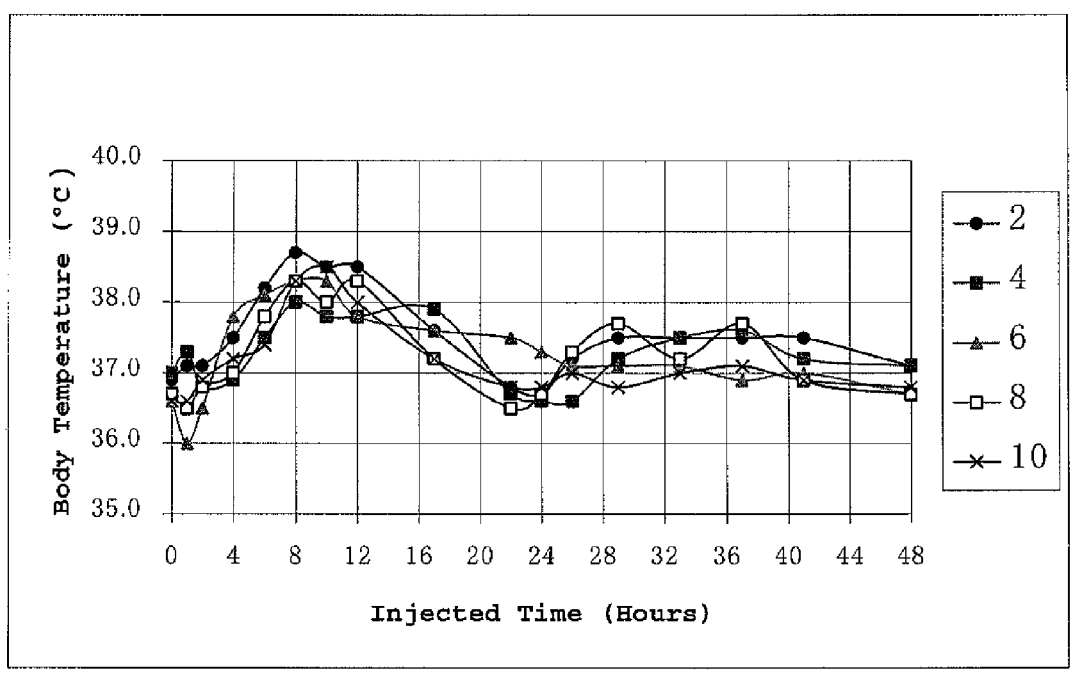
Figures 2, 8B:
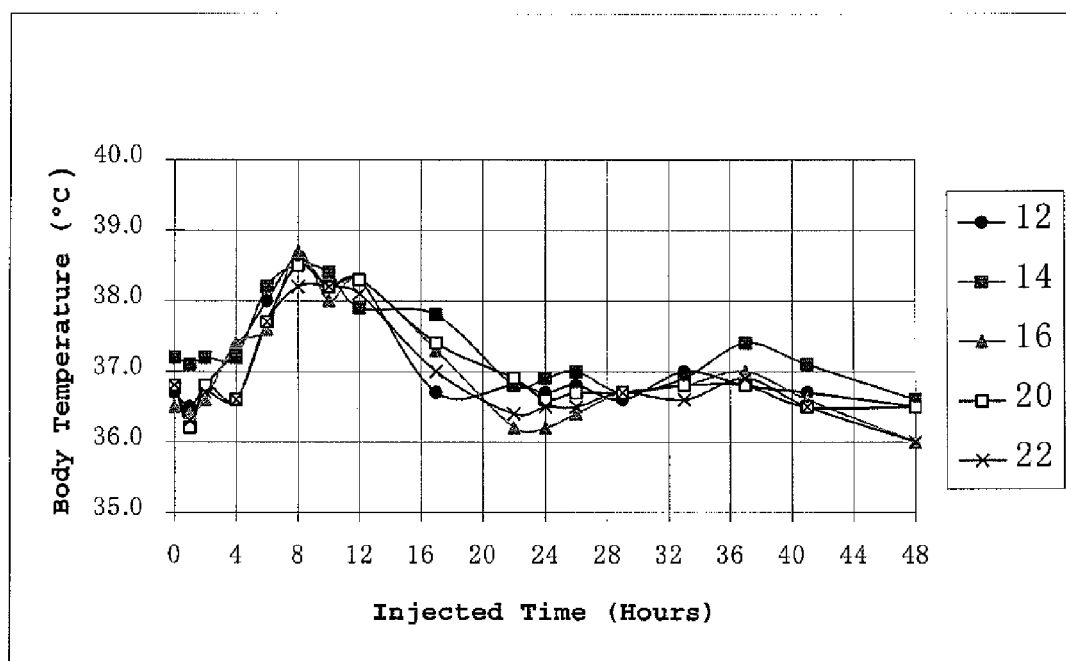

FIG. 8B-1. Curves of Changes of Body Temperature in Group B (5 patients)

This figure is the record of body temperature changes of 5 patients in Group B.

FIG. 8B-2. Curves of Changes of Body Temperature in Group B (5 patients)

This figure is the record of body temperature changes of the other 5 patients in Group B.

Figure 9:
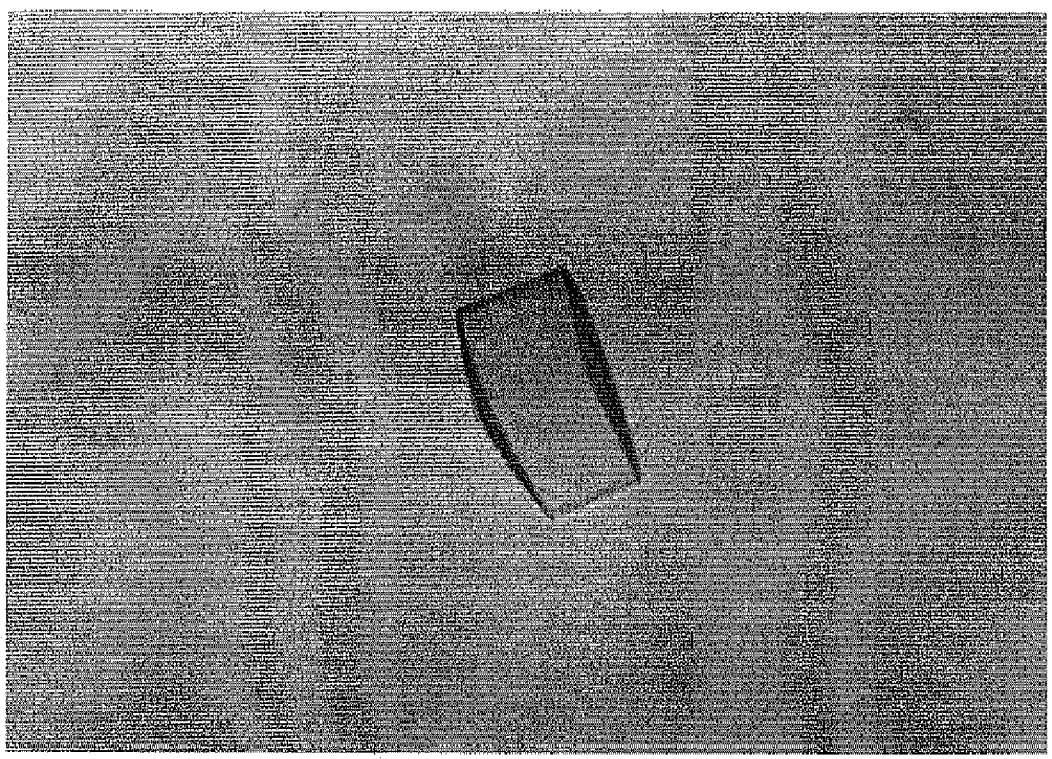
Figure 10:
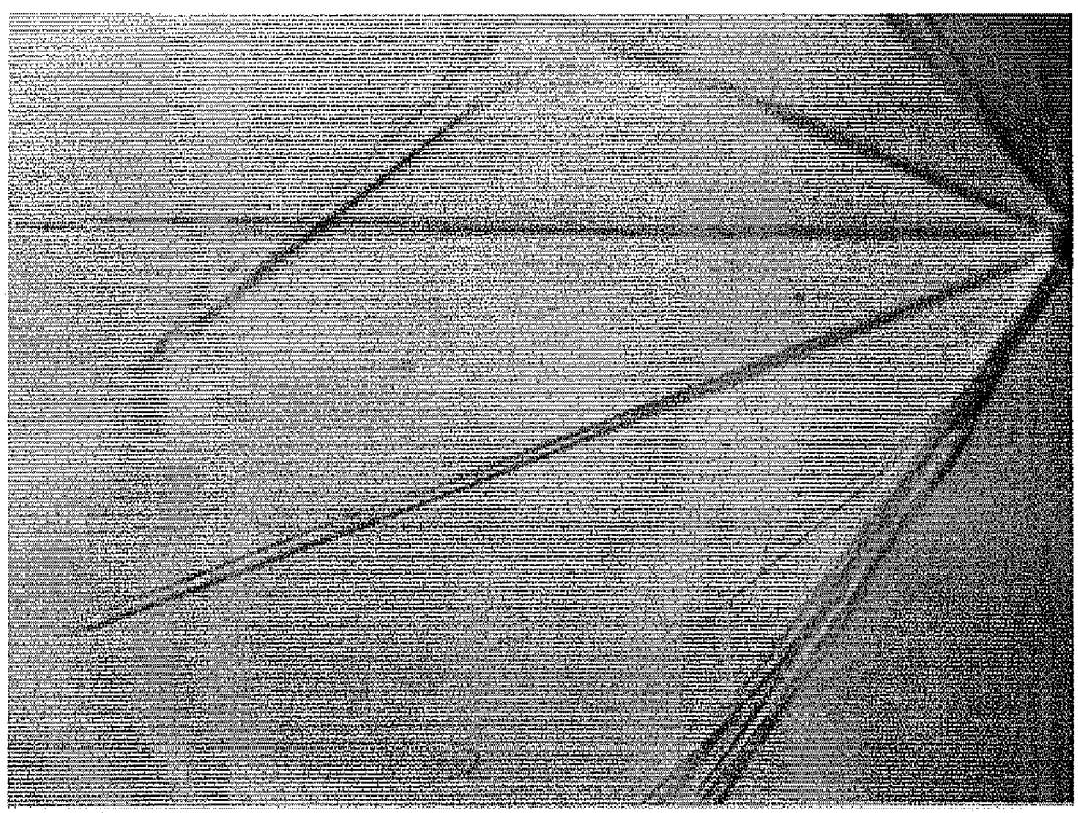
Figure 11:
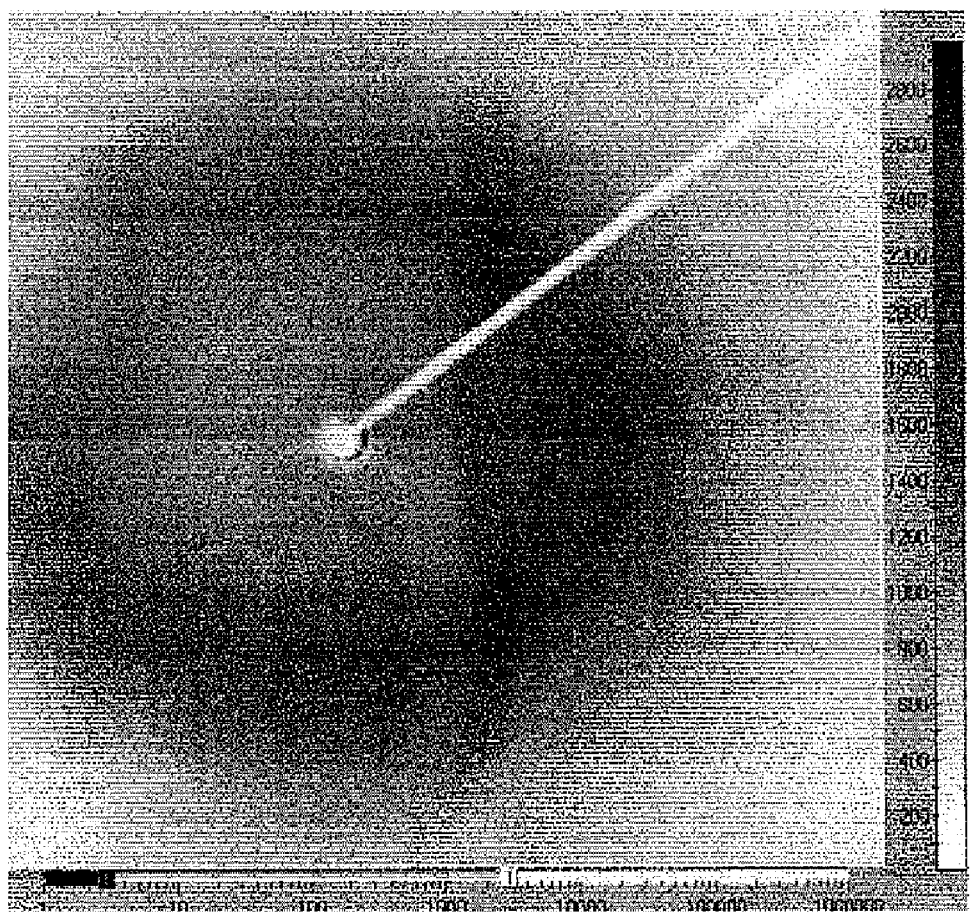

FIG. 9. rsIFN-co Crystal I
FIG. 10. rsIFN-co Crystal II
FIG. 11. The X-ray Diffraction of rsIFN-co Crystal

DETAILED DESCRIPTION OF THE INVENTION

This invention provides a method for producing a recombinant super-compound interferon with changed spatial configuration and enhanced antiviral activity comprising steps of:
(a) Introducing nucleic acid molecule which codes for said interferon with preferred codons for expression to an appropriate host; and
(b) Placing the introduced host in conditions allowing expression of said interferon.

This invention provides the method for producing interferon, further comprising recovery of the expressed interferon.

This invention provides a recombinant super-compound interferon or an equivalent thereof with changed spatial configuration. This invention reveals that proteins with the same primary sequence might have different biological activities. As illustrated in the following example, this invention discloses two proteins with identical amino acid sequences but with different activities. The efficacy of this activity may sometimes be improved and, sometimes, the protein with changed spatial configuration would reveal new function.

An equivalent is a molecule which is similar in function to the compound interferon. An equivalent could be a deletion, substitution, or replacement mutant of the original sequence. Alternatively, it is also the intention of this invention to cover mimics of the recombinant super-compound interferon. Mimics could be a peptide, polypeptide or a small chemical entity.

The interferon described herein includes but is not limited to interferon α, β, or ω. In an embodiment, it is IFN-1a, IFN-2b or other mutants. In an embodiment, the super-compound interferon disclosed has higher efficacy than the interferon described in U.S. Pat. Nos. 4,695,623 or 4,897,471. This super-compound interferon is believed to have unique secondary or tertiary structure. (See e.g. FIG. 6.)

The super-compound interferon described herein has spatial structure change(s) resulting from the changes of its production process.

The above-described super-compound interferon may be produced by a high-efficiency expression system which uses a special promoter. In an embodiment, the promoter is $P_{BAD}$. As could be easily appreciated by other ordinary skilled artisans. Other inducible promoters, such as heat shock promoters or heavy metal inducible promoters, may be used in this invention.

The super-compound interferon may also be produced with its gene as artificially synthesized cDNA with adjustment of its sequence from the wild-type according to codon preference of *E. Coli*. Extensive discussion of said codon usage (preference) may be found in U.S. Pat. No. 4,695,623. See e.g. column 6, line 41-column 7, line 35.

The above-described super-compound interferon possesses anti-viral or anti-tumor activity, and; therefore, is useful in inhibiting, preventing and treating viral diseases, tumors, or cancers.

As used herein, viral diseases include, but are not limited to, hepatitis A, hepatitis B, hepatitis C, other types of hepatitis, infections caused by Epstein-Barr virus, Cytomegalovirus, herpes simplex viruses, other herpes viruses, papovaviruses, poxviruses, picornaviruses, adenoviruses, rhinoviruses, human T-cell leukemia virus I, human T-cell leukemia virus II, or human T-cell leukemia virus III.

Viral upper respiratory infection, alternative names common cold, colds. This is a contagious viral infection of the upper respiratory tract characterized by inflammation of the mucous membranes, sneezing, and a sore throat. It is usually caused by over 200 different viruses, known as rhinoviruses. Colds are not caused by the same viruses responsible for influenza. Colds are spread through droplets from the coughing or sneezing of others with a cold or by hand contact with objects contaminated by someone with a cold. The incidence of colds is highest among children, and the incidence decreases with age because immunity to the virus causing the cold occurs after the illness. Gradually, immunity to a wide variety of viruses that cause colds is developed in adults. Children may have 10 colds a year, and adults may have 3 colds a year.

The U.S. Centers for Disease Control and Prevention have estimated that the average annual incidence of upper respiratory tract infections (URIs) in the United States is 429 million episodes, resulting in more than $2.5 billion in direct and indirect healthcare costs.

The common cold is most often caused by one of several hundred rhinoviruses (52%), but coronaviruses (8%) or the respiratory syncytial virus (7%) may also lead to infection. Other viruses, such as influenza (6%), parainfluenza, and adenoviruses, may produce respiratory symptoms, but these are often associated with pneumonia, fever, or chills.

Colds occur in a seasonal pattern that usually begins in mid-September and concludes in late April to early May. The common cold is quite contagious and can be transmitted by either person-to-person contact or airborne droplets. Upper respiratory symptoms usually begin 1 to 2 days after exposure and generally last 1 to 2 weeks, even though viral shedding and contagion can continue for 2 to 3 more weeks. Symptoms may persist with the occurrence of complications such as sinusitis or lower respiratory involvement such as bronchitis or pneumonia.

The common cold has a variety of overt symptoms, including malaise, nasal stuffiness, rhinorrhea, nonproductive cough, mild sore throat, and, in some cases, a low-grade fever. Because of the similarity of symptoms, a cold may be mistaken for perennial allergic rhinitis, but allergies can usually be ruled out because of the differences in chronicity.

If a patient presents with a viral URI, the spectrum of remedies is extensive. Since most of these infections are self-limiting, clinicians usually recommend rest and fluids, but other treatments include environmental and nutritional therapies, over-the-counter and prescription decongestant and antihistamine products, new antihistamine and anticholinergic nasal formulations, and antibiotics. Table 1 lists commonly used cough and cold medications and their side effects.

TABLE 1

A Profile of Common Cough and Cold Medications and their side effects

| Medication | Purpose | Side Effects and Special Considerations |
|---|---|---|
| Aerosolized beta2 agonists (eg, albuterol) | Reverse postinflammatory bronchospasm | Raises heart rate and may cause tremor |
| Alcohol-based liquid combination products | Treat multiple symptoms | Potential drowsiness and coordination problems |
| Alphal agonists (oral) (eg, pseudoephedrine, phenylpropanolamine) | Decongestion | May cause tachycardia, nervousness, transient stimulation, dizziness, drowsiness, elevation of blood pressure |
| Anticholinergic compounds: Ipratropium bromide (topical) | Drying | May cause nasal dryness and occasional epistaxis |
| Other anticholinergics (eg, methscopolamine, atropine, hyoscyamine) | Drying | May cause orthostasis, dysfunction of heat regulation, dry mouth, constipation |
| Antihistamines (oral) (eg, chlorpheniramine, diphenhydramine) | Drying | Drowsiness, dry mouth, orthostatic hypertension |
| Benzonatate capsules | Cough suppression, local anesthesia | Chewing can numb the mouth; can cause sedation, dizziness |
| Codeine, hydrocodone | Cough suppression | Drowsiness, constipation, nausea |
| Dextromethorphan | Cough suppression | Drowsiness possible, but side effects uncommon |
| Guaifenesin | Promote expectoration (mucolysis) | No side effects; must be taken with lots of water to improve efficacy |
| Topical decongestants (eg, oxymetazoline, phenylephrine) | Decongestion | Local burning; prolonged use may cause dependence |
| Zinc and vitamin C lozenges | Possible reduction in symptom severity and duration | Possible taste disturbance, increase of oxalate stones if susceptible |

Usage of Super-Compound Interferon to Prevent or Treat URI

Nearly 70~80% URI are caused by viruses such as respiratory Syncytical virus, adenovirus, rhinovirous, cox-sackie virus, corona virus and its variant, influenza A virus and its variant, influenza B virus and its variant, parainfluenza virus and its variant, or enterovirus and its variant. A main cause of URI in adults is from rhinovirous. For children, respiratory syncytical virus and parainfluenza virus are two leading causes of URI.

Super-compound interferon plays an important role in the fight against viruses that cause URI. Super-compound interferon gains its anti-virus affects mainly via two mechanisms:
1. Attach to surface of sensitive cells and induce them to product anti-virus protein, then block the duplication and reproduction of viruses in vivo.
2. Super-compound interferon can adjust immune response, including T-cell immune response, activity of NK cell, the phagocytosis function of monokaryon, and even formation of some antibodies in vivo.

In treatment for URI, Super-compound interferon can be directly applied to the affected area via a spray inspiration. This method of treatment allows the interferon to reach the target cells first hand. Consequently, marketing the supply as a spray, rather than via oral or injection, would be safer and more effective for administrating the interferon.

Usage of Super-Compound Interferon to Prevent or Treat SARS

With the consent of the Sichuan working group on SARS prevention and control, the distribution of Super-compound interferon began in May of 2003. Super-compound interferon spray was allocated to doctors and nurses in hospitals, populated areas with a high risk for SARS, and to the National research group on prevention and control of SARS. Among the 3,000 users as of Dec. 19, 2003, there were no reports of any side effects connected to the use of the spray. Furthermore, none of the doctors and nurses, the people of Sichuan Province, or other organizations that have used the Super-compound interferon spray has been infected by SARS.

Therefore, this invention provides a method for inhibiting, preventing or treating virus replication or virus-infected cells by contacting said virus or infected cells with an effective amount of the super-compound interferon or its equivalent.

This super-compound interferon is useful in inhibiting, preventing or treating the following cancers or tumors:

TABLE 2

| Cancer | Skin Cancer | Basal Cell Carcinoma |
|---|---|---|
|  |  | Malignant Melanoma |
|  | Renal cell carcinoma |  |
|  | Liver Cancer |  |
|  | Thyroid Cancer |  |
|  | Rhinopharyngeal Cancer |  |
|  | Solid Carcinoma | Prostate Cancer |
|  |  | Stomach/Abdominal Cancer |
|  |  | Esophageal Cancer |
|  |  | Rectal Cancer |
|  |  | Pancreatic Cancer |
|  |  | Breast Cancer |
|  | Ovarian Cancer & Superficial Bladder Cancer |  |
|  | Hemangioma |  |
|  | Epidermoid Carcinoma | Cervical Cancer |
|  |  | Non-small Cell Lung Cancer |
|  |  | Small Cell Lung Cancer |
|  |  | Glioma |
| Malignant Hemal Disease | Leucocythemia | Acute Leucocythemia |
|  |  | Chronic Leucocythemia |
|  | Chronic Myelocytic Leukemia |  |
|  | Hairy Cell Leukemia |  |
|  | Lymphadenoma |  |
|  | Multiple Myeloma |  |
|  | Polycythemia Vera |  |
| Others | Kaposi's Sarcoma |  |

Patient #1. A female patient with ovarian cancer started receiving injections. She received 15 μg injections on July 14th, July 16th, July 18th, July 20th, and July 22nd. On July 14th, 2000 ml of peritoneal fluid was observed. The patient underwent chemotherapy on July 22$^{nd}$. On August 3$^{rd}$, the patient's peritoneum was opened. 2 l of fluid was expected to be found, but only 200 ml of fluid was observed. The left and right ovaries and lymphatic nodes were cancerous. All other organs were clear.

Patient #2. A kidney cancer patient was treated in the following manner. In a half-month period, the patient was given 3 injections of 9 μg of rSIFN-co and 3 injections of 15 μg of rSIFN-co. In the one full month following these injections, he received 9 μg and 15 μg injections of rSIFN-co every other day. A kidney biopsy showed no metastasis after this course of treatment. The patient showed a full recovery. Every half year after recovery, the patient received 15 μg injections of rSIFN-co 15 times over a one-month period.

Accordingly, this invention provides a method for inhibiting tumor or cancer cell growth by contacting the super-compound interferon or its equivalent with said tumor or cancer cells.

In a further embodiment, the super-compound interferon inhibits the DNA duplication and secretion of HBsAg and HBeAg of Hepatitis B Virus.

This invention also provides an artificial gene which codes for the super-compound interferon or its equivalent. It is within the ordinary skill. to design an artificial gene. Many methods for generating nucleotide sequence and other molecular biology techniques have been described previously. See for example, Joseph Sambrook and David W. Russell, Molecular Cloning: A laboratory Manual, December 2000, published by Cold Spring Harbor Laboratory Press.

This invention provides a vector comprising the gene which codes for the super-compound interferon or its equivalent.

This invention provides an expression system comprising the vector comprising the gene which codes for the super-compound interferon or its equivalent. The cells include, but are not limited to, prokaryotic or eukaryotic cells.

This invention also provides a host cell comprising the vector comprising the gene which codes for the super-compound interferon or its equivalent.

This invention provides a process for production of recombinant super-compound interferon comprising introducing an artificial gene with selected codon preference into an appropriate host, culturing said introduced host in an appropriate condition for the expression of said compound interferon and harvesting the expressed compound interferon.

The process may comprise extraction of super-compound interferon from fermentation broth, collection of inclusion body, denaturation and renaturation of the harvested protein.

The process may maintain the high efficacy even when the super-compound interferon is used with an agent and in a particular concentration. The process also comprises separation and purification of the super-compound interferon. The process further comprises lyophilization of the purified super-compound interferon. The process comprises production of liquid injection of super-compound interferon.

This invention also provides the produced super-compound interferon by the above processes.

This invention provides a composition comprising the recombinant super-compound interferon or its equivalent and a suitable carrier.

This invention provides a pharmaceutical composition comprising the recombinant super-compound interferon or its equivalent and a pharmaceutically acceptable carrier.

This invention provides a method for treating or preventing viral diseases or tumors in a subject comprising administering to the subject an effective amount of the super-compound interferon or its equivalent.

This invention provides the above-described method wherein the viral diseases include, but are not limited to, hepatitis A, hepatitis B, hepatitis C, other types of hepatitis, infections of viruses caused by Epstein-Barr virus, Cytomegalovirus, herpes simplex viruses, or other type of herpes viruses, papovaviruses, poxviruses, picornaviruses, adenoviruses, rhinoviruses, human T-cell leukemia viruses I, or human T-cell leukemia viruses II, or human T-cell leukemia virus III.

This invention provides the above-described method wherein super-compound interferon was administered orally, via vein injection, muscle injection, peritoneal injection, subcutaneous injection, nasal or mucosal administration, or by inhalation via an inspirator.

This invention provides the above-described method wherein super-compound interferon was administered following the protocol of injection: 9 μg or 15 μg every two days, 3 times a week, for 24 weeks.

It was surprising to find that rSIFN-co, the spatial structure of which has been changed, is not only a preparation to inhibit the DNA duplication of hepatitis B, but to inhibit the secretion of HBsAg and HBeAg on 2.2.15 cells.

One objective of this invention is to offer a preparation of rSIFN-co to directly inhibit the DNA duplication of hepatitis B viruses and the secretion of HBeAg and HBsAg of hepatitis B and decrease them to normal levels.

In one embodiment, rSIFN-co was produced with recombinant techniques. On the condition of fixed amino acid sequence, the IFN DNA was redesigned according to the E. Coli. codon usage and then the rSIFN-co gene was artificially synthesized. rSIFN-co cDNA was cloned into the high-expression vector of E. Coli. by DNA recombinant techniques, and a high expression of rSIFN-co was gained by using of induce/activate-mechanism of L-arabinose to activate the transcription of $P_{BAD}$ promoter.

Compared with usual thermo-induction, pH induction and IPTG induction systems of genetic engineering, arabinose induction/activation system has some advantages: (1) Common systems relieve promoter function by creating a "derepression" pattern. Promoters then induce downstream gene expression. So temperature and pH change and the addition of IPTG cannot activate promoters directly. In the system disclosed herein, L-arabinose not only deactivates and represses but also activates the transcription of $P_{BAD}$ promoter which induces a high expression of rSIFN-co. Therefore, the arabinose induction/activation system is a more effective expression system. (2) The relationship between Exogenous and L-arabinose dosage is linear. This means the concentration of arabinose can be changed to adjust the expression level of the exogenous gene. Therefore, it is easier to control the exogenous gene expression level in E. Coli. by arabinose than by changing temperature and pH value. This characteristic is significant for the formation of inclusion bodies. (3) L-arabinose is resourceful, cheap and safe, which, on the contrary, are the disadvantages of other inducers such as IPTG.

This embodiment creates an effective and resistant rSIFN-co-expressing E. Coli. engineering strain with an L-arabinose induction/activation system. The strain is cultivated and fermented under suitable conditions to harvest the bacterial bodies. Inclusion bodies are then purified after destroying bacteria and washing repeatedly. The end result, mass of high-purity, spatial-configuration-changed rSIFN-co protein for this invention and for clinical treatment, was gained from denaturation and renaturation of inclusion bodies and a series of purification steps. The following are some rSIFN-co preparations: tablets, capsules, liquids for oral consumption, pastes, injections, sprays, suppositories, and solutions. Injections are recommended. It is common to subcutaneously inject or vein-inject the medicine. The medicine carrier could be any acceptable medicine carrier, including carbohydrates, cellulosum, adhesive, collapse, emollient, filling, add-dissolving agent, amortization, preservative, thickening agent, matching, etc.

This invention also provides a pharmaceutical composition comprising the above composition and a pharmaceutically acceptable carrier.

For the purposes of this invention, "pharmaceutically acceptable carriers" means any of the standard pharmaceutical carriers. Examples of suitable carriers are well known in the art and may include, but are not limited to, any of the standard pharmaceutical carriers, such as a phosphate buffered saline solution and various wetting agents. Other carriers may include additives used in tablets, granules, capsules, etc. Typically such carriers contain excipients such as starch, milk, sugar, certain types of clay, gelatin, stearic acid or salts thereof, magnesium or calcium stearate, talc, vegetable fats or oils, gum, glycols or other known excipients. Such carriers may also include flavor and color additives or other ingredients. Compositions comprising such carriers are formulated by well-known conventional methods.

This invention provides a method for preventing or treating Severe Acute Respiratory Syndrome, or virus-induced upper respiratory diseases, of a subject comprising administering to the subject an effective amount of recombinant super-compound interferon or a functional equivalent thereof.

In an embodiment of the above method, the interferon is α, β, or ω.

The super-compound interferon may be administered orally, via vein injection, muscle injection, peritoneal injection, subcutaneous injection, nasal or mucosal administration, or by inhalation via an inspirator.

In an embodiment, the interferon is delivered by a spray device.

In a specific embodiment, the device is described in FIG. 7.

In one of the embodiments, the interferon is lyophilized.

This invention provides a method for inhibiting the causative agent of Severe Acute Respiratory Syndrome, or virus-induced upper respiratory diseases, comprising contacting the agent with an effective amount of super-compound interferon or its equivalent.

It is determined that the causative agent of SARS is a virus. See eg. Rota et al (2003), Characterization of a Novel Coronavirus Associated with Severe Acute Respiratory Syndrome. Science 1085952 and Marra, et al. (2003), The Genome Sequence of the SARS-Associated Coronavirus. Science 1085853.

This invention also provides a method for inhibiting Severe Acute Respiratory Syndrome virus or Severe Acute Respiratory Syndrome virus-infected cells, or virus-induced upper respiratory diseases, or cells infected with viruses capable of inducing upper respiratory diseases, comprising contacting an effective amount of the super-compound interferon with said virus or cell. This contact could be direct or indirect.

This invention provides a composition comprising an effective amount of the super-compound interferon capable of inhibiting Severe Acute Respiratory Syndrome virus or Severe Acute Respiratory Syndrome virus-infected cells, or virus-induced upper respiratory diseases, or cells infected with viruses capable of inducing upper respiratory diseases, and a suitable carrier.

This invention provides a composition comprising an effective amount of the super-compound interferon capable of preventing or treating Severe Acute Respiratory Syndrome, or virus-induced upper respiratory diseases, of a subject and a suitable carrier.

This invention provides a pharmaceutical composition comprising an effective amount of the recombinant super-compound interferon capable of inhibiting Severe Acute Respiratory Syndrome virus or Severe Acute Respiratory Syndrome virus-infected cells, or virus-induced upper respiratory diseases, and a pharmaceutically acceptable carrier.

This invention provides a pharmaceutical composition comprising an effective amount of the recombinant super-compound interferon capable of preventing or treating Severe Acute Respiratory Syndrome, or virus-induced upper respiratory diseases, in a subject and a pharmaceutically acceptable carrier.

This invention provides a device to deliver the above-described pharmaceutical composition.

In a preferred embodiment, the subject is a human. As it can easily be appreciated, the super-compound interferon can be used in other animals or mammals.

This invention provides a method for preventing Severe Acute Respiratory Syndrome or virus-induced upper respiratory diseases, in humans comprising application of the super-compound interferon three times a day via a spray which contains twenty micrograms of interferon, equal to ten million units of activity in three milliliter.

This invention will be better understood from the examples which follow. However, one skilled in the art will readily appreciate that the specific methods and results discussed are merely illustrative of the invention as described more fully in the claims which follow thereafter.

EXPERIMENTAL DETAILS

EXAMPLE 1 rSIFN-co is a new interferon molecule constructed according to conservative amino acid in human IFN-α subtype with genetic engineering method. It has been proven that rSIFN-co has broad-spectrum IFN activity, such as high antivirus and tumor inhibition activity, especially for effectively treating hepatitis C.

E. Coli. codon was used to redesign rSIFN-co cDNA and then artificially synthesize cDNA of rSIFN-co from published rSIFN-co DNA sequences and deduced amino acid sequences (FIG. 1).

In order to get pure rSIFN-co protein, rSIFN-co cDNA was cloned into E. Coli. high-expression vector, and L-arabinose, which can activate strong $P_{BAD}$ promoter in vectors, was used to induce high expression of rSIFN-co gene.

Synthesis of E. Coli. CDNA Sequence

Redesign of rSIFN-co cDNA Sequence rSIFN-co cDNA was redesigned according to the codon usage of E. Coli. to achieve high expression in E. Coli. Deduced amino acid sequence from the redesigned cDNA sequence of rSIFN-co is completely coincidental with primitive amino acid sequence of published rSIFN-co (FIG. 1).

rSIFN-co cDNA Sequence Synthesis rSIFN-co CDNA 5'- Terminus and 3'- Terminus Semi-Molecular Synthesis Two semi-moleculars can be directly synthesized: rSIFN-co cDNA 5'-terminus 280 bp (fragment I) and 3'-terminus 268 bp(fragment II) by PCR. There are 41 bp overlapping among fragment II and fragment I.

(1) Chemical synthesis oligodeoxynucleotide fragment:

```
Oligomer A:                                 (SEQ ID NO:5)
5'ATGTGCGACCTGCCGCAGACCCACTCCCTGGGTAACCGTCGTGCTCTG

ATCCTGCTGGCTCAGATGCGTCGTATCTCCCCGTTCTCCTGCCTGAAAGA

CCGTCACGAC3'

Oligomer B:                                 (SEQ ID NO:7)
5'CTGAAAGACCGTCACGACTTCGGTTTCCCGCAGGAGAGGTTCGACGGT

AACCAGTTCCAGAAGCTCAGGCTATCTCCGTTCTGCACGAAATGATCCAG

CAGACCTTC3'

Oligomer C:                                 (SEQ ID NO:8)
5'GCTGCTGGTACAGTTCGGTGTAGAATTTTTCCAGCAGGGATTCGTCCC

AAGCAGCGGAGGAGTCTTTGGTGGAGAACAGGTTGAAGGTCTGCTGGATC

ATTTC3'

Oligomer D:                                 (SEQ ID NO:9)
5'ATCCCTGCTGGAAAAATTCTACACCGAACTGTACCAGCAGCTGAACGA

CCTGGAAGCTTGCGTTATCCAGGAAGTTGGTGTTGAAGAAACCCCGCTGA

TGAAC3'

Oligomer E:                                (SEQ ID NO:10)
5'GAAGAAACCCCGCTGATGAACGTTGACTCCATCCTGGCTGTTAAAAAA

TACTTCCAGCGTATCACCCTGTACCTGACCGAAAAAAAATACTCCCCGTG

CGCTTGGG3'

Oligomer F:                                (SEQ ID NO:11)
5'TTATTCTTTACGACGCAGACGTTCCTGCAGGTTGGTGGACAGGGAGAA

GGAACGCATGATTTCAGCACGAACAACTTCCCAAGCGCACGGGGAGTATT

TTTTTTCGGTCAGG3'
```

PCR I for Fragment I: oligodeoxynucleotide B as template, oligodeoxynucleotide A and C as primers, synthesized 280 bp Fragment I.

| PCR I mixture | (units: μl) |
|---|---|
| sterilized distilled water | 39 |
| 10 × Pfu buffer (Stratagen American Ltd.) | 5 |
| dNTP mixture (dNTP concentration 2.5 mmol/L) | 2 |
| Oligomer A primer (25 μmol/L) | 1 |
| Oligomer C primer (25 μmol/L) | 1 |
| Oligomer B template (1 μmol/L) | 1 |
| Pfu DNA polymerase (Stratagen American Ltd.) (25 U/μl) | 1 |
| Total volume | 50 μl |

PCR cycle: 95 I
2 m → (95° C. 45 s → 65° C. 1 m → 72° C. 1 m) × 25 cycle → 72° C. 10 m → 4° C.

PCR II for Fragment II: oligodeoxynucleotide E as template, oligodeoxynucleotide D and F as primers, synthesized 268 bp Fragment II.

| PCR II mixture | (units: μl) |
|---|---|
| sterilized distilled water | 39 |
| 10 × Pfu buffer (Stratagen American Ltd.) | 5 |
| dNTP mixture (dNTP concentration 2.5 mmol/L) | 2 |
| Oligomer D primer (25 μmol/L) | 1 |
| Oligomer F primer (25 μmol/L) | 1 |
| Oligomer E template (1 μmol/L) | 1 |
| Pfu DNA polymerase (Stratagen American Ltd.) (25 U/μl) | 1 |
| Total volume | 50 μl |

PCR cycle: the same as PCR I

Assembling of rSIFN-co cDNA

Fragment I and II were assembled together to get the complete cDNA molecular sequence of rSIFN-co using the overlapping and extending PCR method. Restriction enzyme Nde I and Pst I were introduced to clone rSIFN-co cDNA sequence into plasmid.

(1) Chemical synthesis primers

```
Oligomer G:                                (SEQ ID NO:12)
5'ATCGGCCATATGTGCGACCTGCCGCAGACCC3'

Oligomer H:                                (SEQ ID NO:13)
5'ACTGCCAGGCTGCAGTTATTCTTTACGACGCAGACGTTCC3'
```

(2) Overlapping and extending PCR

| PCR mixture | (units: μl) |
|---|---|
| sterilized distilled water | 38 |
| 10 × Pfu buffer (Stratagen American Ltd.) | 5 |
| dNTP mixture (dNTP concentration 2.5 mmol/L) | 2 |
| primer G (25 μmol/L) | 1 |
| primer H (25 μmol/L) | 1 |
| *fragment I preduction (1 μmol/L) | 1 |
| *fragment II preduction (1 μmol/L) | 1 |
| Pfu DNA polymerase (Stratagen American Ltd.) (2.5 U/μl) | 1 |
| Total volume | 50μ |

*Separate and purify PCR production with StrataPrep PCR purification kit produced by Stratagen American Ltd. And dissolve into sterilized distilled water.
PCR cycle: the same as PCR I rSIFN-co Gene Clone and Sequence Analysis pLac T7 plasmid as cloning vector. pLac T7 plasmid is reconstructed with pBluescript II KS(+) plasmid produced by Stratagen (FIG. 3).

Purified PCR production of rSIFN-co cDNA with StrataPrep PCR purification kit. Digest cDNA and pLac T7 plasmid with NdeI and PstI. Run 1% agarose gel electrophoresis and separate these double-digested DNA fragments. Recover 507 bp long rSIFN-co DNA fragment and 2.9 kb plasmid DNA fragment. Ligate these fragments by T4 DNA ligase to form a recombinant plasmid. Transform $DH_{5\alpha}$competent cells (Gibco) with the recombinant plasmid, culture at 37° C. overnight. Identify the positive recombinant colony, named pHY-1.

Run DNA sequencing with SequiTherm™ Cycle Sequencing Kit produced by American Epicentre Technologies Ltd using L1-COR Model 4000L. Primers are T7 and T3 common sequence primer, the DNA sequencing result matches theoretic design.

Purify the rSIFN-co, sequence the N-terminus amino acids, the N-terminus amino acid sequence matches experimental design which is as follows:

(SEQ ID NO:14)
N-Cys-Asp-Leu-Pro-Gln-Thr-His-Ser-Leu-Gly-Asn-Arg-
Arg-Ala-Leu- Construction, Transformation, Identification, and Hereditary Stability of Expression Vector Construction and Transformation of Expression Vector Digested E. Coli. expression vector pHY-4 (see FIG. 3) with Nde I to linearize and subsequently digest with Xba I. Run 1% agarose gel electrophoresis, and purify the 4.8 kb pHY-4 Nde I -Xba I digest fragment with QIAEX II kit produced by QIAGEN Germany Ltd.

At the same time, the pHY-4 plasmid is double digested with Nde I-Xba I. Run 1% agarose gel electrophoresis and purify the 715 bp fragment. Ligate the rSIFN-co and pHY-4 fragments with T4 DNA ligase to construct the recombinant plasmid (See FIG. 4). Transform $DH_{5\alpha}$ competent cells with the recombinant plasmid. Spread the transformed cells on LB plate with Amp, 37° C. culture overnight.

Positive Cloning Strain Screening

Randomly choose E. Coli. colonies from above LB-plate, screening the positive strains containing recombinant vector by endonuclease digesting and PCR analysis. Name one of the positive recombinant plasmid pHY-5, and name the strain containing pHY-5 plasmid PVIII. Amplify and store the positive strain with glycerol in –80° C.

High Expression of rSIFN-co Gene in E. Coli.

In pHY-5 plasmid, rSIFN-co gene is under control of strong promoter $P_{BAD}$. This promoter is positively and negatively regulated by the product of the gene araC. AraC is a transcriptional regulator that forms a complex with arabinose. In the absence of arabinose, the AraC dimer binds $O_2$ and $I_1$ forming a 210 bp loop. This conformation leads to a complete inhibition of transcription. In the presence of arabinose, the dimer is released from $O_2$ and binds $I_1$ and $I_2$ leading to transcription. Arabinose binding deactivates, represses and even activates the transcription Of $P_{BAD}$ promoter, which stimulates $P_{BAD}$ inducing high expression of rSIFN-co rSIFN-co expression level in PVIII is more than 50% of the total E. Coli. protein.

SUMMARY

RSIFN-CO is a new interferon molecule artificially built according to the conservative amino acid of human α interferons. It has been proven as a effective anti-hepatitis drug. In order to get enough pure rSIFN-co protein, a stable recombinant E. Coli. strain which high expresses rSIFN-co protein was constructed.

First, according to published rSIFN-co amino acid sequence, E. Coli. codon was used to synthesize whole cDNA of rSIFN-co. This DNA fragment was sequenced and proved that the 501 bp codon sequence and TAA termination codon sequence are as expected and consistent with the experimental design. Subsequent analysis revealed that the N-terminus amino acid sequence and amino acid composed of rSIFN-co produced by the recombinant strain were both consistent with the prediction.

The rSIFN-co cDNA was cloned into E. Coli. high-expression vector pHY-4 plasmid to construct the recombinant plasmid pHY-5. E. Coli. LMG194 strain was further transformed with pHY-4 plasmid to get stable rSIFN-co high-expression transformant. This transformant was cultured for 30 generations. The heredity of pHY-5 recombinant plasmid in E. Coli. LMG194 was normal and stable, and the expression of rSIFN-co was high and steady.

E. Coli. LMG194, which contains recombinant pHY-5 plasmid, is actually an ideal high-expression engineering strain.

REFERENCES

1. Blatt L M, Davis J M, Klein S B. et al. The biologic activity and molecular characterization of a novel synthetic interferon-alpha species, consensus interferon. Journal of Interferon and Cytokine Research, 1996;16 (7): 489-499.
2. Alton, K. et al: Production characterization and biological effects of recombinant DNA derived human IFN-α and IFN-γ analogs. In: De Maeger E, Schellekens H. eds. The Biology of Interferon System.2nd ed. Amsterdam: Elsevier Science Publishers, 1983: 119-128
3. Pfeffer L M. Biologic activity of natural and synthetic type 1 interferons. Seminars in Oncology, 1997;24 (3 suppl 9): S9-63--S9-69.
4. Ozes O N, Reiter Z, Klein S, et al. A comparison of interferon-con1 with natural recombinant interferons-(:antiviral, antiproliferative, and natural killer-inducing activities. J. Interferon Res., 1992; 12:55-59.
5. Heathcote E J L, Keeffe E B, Lee S S, et al. Re-treatment of chronic hepatitis C with consensus interferon. Hepatology, 1998;27 (4): 1136-1143.
6. Klein M L, Bartley T D, Lai P H, et al. Structural characterization of recombinant consensus interferon-alpha. Journal of Chromatography, 1988; 454:205-215.
7. The Wisconsin Package, by Genetics Computer Group, Inc. Copyright 1992, Medison, Wis., USA
8. Nishimura, A et al: A rapid and highly efficient method for preparation of competent E. coli cells. Nuclei. Acids Res. 1990, 18:6169
9. All molecular cloning techniques used are from: Sambrook, J., E. F. Fritsch and T. Maniatis. Molecular Cloning: A laboratory manual, 2nd ed. CSH Laboratory Press, Cold Spring Harbour, N.Y. 1989.
10. Guzman, L. M et al: Tight regulation, modulation, and high-level express-ion by vectors containing the arabinose PBAD promoter. J. Bacteriol. 1995, 177: 4121~4130.

rSIFN-co cDNA Sequence Designed According to E.COLI. Condon rSIFN-co cDNA SEQUENCE DESIGNED ACCORDING TO E. COLI. CODON
USAGE AND DEDUCED rSIFN-co AMINO ACID SEQUENCE

```
        5'      11       21       31       41       51
   +1    M  C  D   L  P  Q  T   H  S  L   G  N  R   R  A  L  I  L  L  A
    1  ATGTGCGACC TGCCGCAGAC CCACTCCCTG GGTAACCGTC GTGCTCTGAT CCTGCTGGCT
       TACACGCTGG ACGGCGTCTG GGTGAGGGAC CCATTGGCAG CACGAGACTA GGACGACCGA
```

-continued rSIFN-co cDNA SEQUENCE DESIGNED ACCORDING TO *E. COLI.* CODON
USAGE AND DEDUCED rSIFN-co AMINO ACID SEQUENCE

```
  5'      71        81        91       101       111
+1   Q M R R I S P F S C   L K   D R   H D F   G F P
 61  CAGATGCGTC GTATCTCCCC GTTCTCCTGC CTGAAAGACC GTCACGACTT CGGTTTCCCG
     GTCTACGCAG CATAGAGGGG CAAGAGGACG GACTTTCTGG CAGTGCTGAA GCCAAAGGGC

5'     131       141       151       161       171
+1   Q E E F D   G N Q F Q K   A Q A I S V L H E
121  CAGGAAGAAT TCGACGGTAA CCAGTTCCAG AAAGCTCAGG CTATCTCCGT TCTGCACGAA
     GTCCTTCTTA AGCTGCCATT GGTCAAGGTC TTTCGAGTCC GATAGAGGCA AGACGTGCTT

5'     191       201       211       221       231
+1   M I Q Q T F N   L F S T K   D S S   A A   W D E
181  ATGATCCAGC AGACCTTCAA CCTGTTCTCC ACCAAAGACT CCTCCGCTGC TTGGGACGAA
     TACTAGGTCG TCTGGAAGTT GGACAAGAGG TGGTTTCTGA GGAGGCGACG AACCCTGCTT

5'     251       261       271       281       291
+1   S L L E K F Y   T E L   Y Q Q L N   D L E A C
241  TCCCTGCTGG AAAAATTCTA CACCGAACTG TACCAGCAGC TGAACGACCT GGAAGCTTGC
     AGGGACGACC TTTTTAAGAT GTGGCTTGAC ATGGTCGTCG ACTTGCTGGA CCTTCGAACG

5'               311       321       331       341       351
+1    V   I Q     E V G V     E E T   P   L M N     V   D   S I   L    A
301  GTTATCCAGG AAGTTGGTGT TGAAGAAACC CCGCTGATGA ACGTTGACTC CATCCTGGCT
     CAATAGGTCC TTCAACCACA ACTTCTTTGG GGCGACTACT TGCAACTGAG GTAGGACCGA

5'               371       381       391       401       411
+1    V   K   K     Y   F Q   R   I T     L Y   L   T E K   K Y   S    P   C
361  GTTAAAAAAT ACTTCCAGCG TATCACCCTG TACCTGACCG AAAAAAAATA CTCCCCGTGC
     CAATTTTTTA TGAAGGTCGC ATAGTGGGAC ATGGACTGGC TTTTTTTTAT GAGGGGCACG

5'              431       441       451       461       471
+1   A W   E   V V   R   A E I   M   R   S   F S L   S T   N   L   Q
421  GCTTGGGAAG TTGTTCGTGC TGAAATCATG CGTTCCTTCT CCCTGTCCAC CAACCTGCAG
     CGAACCCTTC AACAAGCACG ACTTTAGTAC GCAAGGAAGA GGGACAGGTG GTTGGACGTC

5'            491       501
+1   E   R   L     R R   K     E     # (SEQ ID NO:2)
481  GAACGTCTGC GTCGTAAAGA ATAA       (SEQ ID NO:1)
     CTTGCAGACG CAGCATTTCT TATT       (SEQ ID NO:15)
```

EXAMPLE 2

Separation and Purification of rSIFN-co

1. Fermentation

Inoculate the recombinant strain in LB media, shaking (200 rpm) under 37° C. overnight (approximate 18 h), then add 30% glycerol to the fermentation broth to get final concentration of 15%, allotted to 1 ml tube and kept in –20° C. as seed for production.

Add 1% of the seed to LB media, shaking (200 rpm) under 37° C. overnight to enlarge the scale of the seed, then add to RM media with a ratio of 10%, culturing under 37° C. Add arabinose (20% solution) to 0.02% as an inductor when the OD600 reaches about 2.0. 4 hours after that, stop the culture process, collect the bacteria by centrifuge, resuspend the pellet with buffer A, and keep in –20° C. overnight. Thaw and break the bacteria by homogenizer, then centrifuge. Wash the pellet with buffer B, buffer C, and distilled water to get a relatively pure inclusion body.

2. Denaturation and Renaturation

Dissolve the inclusion body in Guanidine-HCl (or urea) of 6 mol/L. The solution will be a little cloudy. Centrifuge it at a speed of 10000 rpm. Determine the protein concentration of the supernatant. This supernatant is called "denaturation solution." Add the denaturation solution to renaturation buffer, and keep the final protein concentration under 0.3 mg/ml. It is better to add the totally denaturation solution in three steps instead of one step. Keep the solution overnight under 4° C. Afterwards, dialyze 10 mol/L, 5 mol/L PB buffer and distilled water, then adjust its pH by 2 mol/L HAc-NaAc. Let it stand, then filtrate.

3. Purification

POROS HS/M anion exchange chromatography:

Equivalent column with 20 mmol/L HAc-NaAc (pH 5.0)

↓

Load samples at a speed of 30 ml/min

↓

Wash with 20 CV 20 mmol/L HAc-NaAc (pH 5.0)

↓

5 CV of 0.15 mol / L NaCl + 20 mmol/L HAc-NaAc (pH 5.0) wash

↓

-continued
3 CV of 0.18 mol/L NaCl + 20 mmol/L HAc-NaAc (pH 5.0) wash

↓

0.25 mol/L NaCl + 20 mmol/L HAc-NaAc (pH 5.0) elute target protein

Chelating sepharose™ fast flow: Add PB buffer of 0.2 mol/L(pH 6.6)and NaCl of 4 mol/L in the solution from HS to adjust solution pH to pH 6.0 and NaCl concentration to 1 mol/L.

Column with buffer D

↓

Loading at a rate of 1 ml/min

↓

Wash with buffer E

↓

Wash with buffer F

↓

Elute with buffer G

Condense the eluted solution by POROS HS/M. Sometimes a purification by sephacryl S-100 step can be added to meet stricter purity requirements.

Note:
Buffer A: 100 mmol/L Tris-HCl, pH 7.5-10 mmol/L EDTA-100 mmol/L NaCl
Buffer B: 50 mmol/L Tris-HCl, pH 7.5-1 mol/L Urea-10 mmol/L EDTA-0.5% Triton X-100
Buffer C: 50 mmol/L Tris-HCl, pH 7.5-2 mol/L Urea-10 mmol/L EDTA-0.5% Triton X-100
Buffer D: 1 mol/L NaCl - - - 50 mmol/L $Na_2HPO_4$ (pH 5.5)
Buffer E: 1 mol/L NaCl - - - 50 mmol/L $Na_2HPO_4$ (pH 5.0)
Buffer F: 1 mol/L NaCl - - - 50 mmol/L $Na_2HPO_4$ (pH 4.0)
Buffer G: 1 mol/L NaCl - - - 50 mmol/L $Na_2HPO_4$ (pH 3.6)
Renaturation buffer: 0.5 mol/L Arginine-150 mmol/L Tris-HCl, pH 7.5-0.2 mmol/L EDTA

| | |
|---|---|
| LB Media: | 1 L |
| Tryptone | 10 g |
| Yeast extracts | 5 g |
| NaCl | 10 g |
| RM Media: | 1 L |
| Casein | 20 g |
| MgCl | 1 mmol/L (0.203 g) |
| $Na_2HPO_4$ | 4 g; |
| $KH_2PO_4$ | 3 g, |
| NaCl | 0.5 g |
| $NH_4Cl$ | 1 g |

After purification, the buffer was changed to PBS (pH 7.0) along with the step of condensing by POROS HS/M. This is called the "Protein Stock Solution." It can directly used in the preparation of injections or sprays, or stored at 2-8° C.

| Formula for injection: | Solution | Lyophilized powder |
|---|---|---|
| Solution of rSIFN-co | 34.5 µg/ml | 34.5 µg/ml |
| PB (pH 7.0) | 25 mmol/L | 10 mmol/L |
| Glycine | — | 0.4 mol/L |
| NaCl | 0.1 mol/L | — |
| For spray: | | |
| EDTA | 0.01% | |
| Tween 80 | 0.05% | |
| Trisodium citrate | 10 mmol/L | |
| Glycerol | 1.26% | |
| Sodium Chloride | 0.03% | |
| Phenylmethanol | 0.5% | |
| HSA | 0.1% | |
| rSIF TABLE 3-continued Lowry

| Item of Test | Method |
|---|---|
| Product Appearance Check | |
| Chemical | According to Method in "Chemical and Other Test Methods for Biologics" |
| Test for Specific Activity | According to Method in "Specific Activity Test of Interferon" |
| Sterility Test | According to Method in "c" |
| Abnormal Toxicity Test | Test on Mouse |
| Pyrogen Test | According to Method in "Requirements for Pyrogen Test of Biologics" |
| Test for Stability of Product | |

Note:
"Chemical and Other Test Methods for Biologics", "Requirements for Pyrogen Test of Biologics" and "Requirements for Bacterial Endotoxin Test of Biologics" all can be found in the "Chinese Requirements for Biologics." "Chinese Requirements for Biologics," PAN Zhengan, ZHANG Xinhui, DUAN Zhibing, et al. Chinese Biologics Standardization committee. Published by Chemical Industry Publishing Company, 2000.

EXAMPLE 3

Stability of Lyophilized Powder of Recombinant Super-Compound Interferon Injection The stability experiments were carried out with samples of lyophilized powder of recombinant super-compound interferon (rSIFN-co) injection in two specifications and three batches. The experiments started on April, 2000.

1. Sample Source

Samples were supplied by Sichuan Huiyang Life-engineering Ltd., Sichuan Province. Lot: 990101-03, 990101-05, 990102-03, 990102-05, 990103-03, 990103-05

2. Sample Specifications

Every sample in this experiment should conform with the requirements in the table below.

TABLE 4

Standard of Samples in Experiment

| Items | Standards |
|---|---|
| 1. Appearance | white loose powder |
| 2. Dissolving time | dissolve rapidly in injection water (within 2 min) at room temperature |
| 3. Clarity | colorless liquid or with little milk-like glisten; should not be cloudy, impurity or with indiscernible deposit |
| 4. pH value | 6.5~7.5 |
| 5. Potency (IU/dose) | 80%~150% of indicated quantity (9 µg: 4.5 × $10^6$ IU, 15 µg: 7.5 × $10^6$ IU) |
| 6. Moisture | no more than 3.0% (W/W) |

3. Experimental Content

Test samples at 2~8° C.: The test samples were put into a 2~8° C. refrigerator, then the above items of these samples were respectively tested in the $1^{st}$, $3^{rd}$, $6^{th}$, $9^{th}$, $12^{th}$, $18^{th}$, $24^{th}$, $30^{th}$, $36^{th}$ month. The results were recorded.

Test samples at 25° C.: The test samples were put into a thermostat at 25° C., then the above items of these samples were respectively tested in the $1^{st}$, $3^{rd}$, $6^{th}$, $9^{th}$, $12^{th}$, $18^{th}$, $24^{th}$, $30^{th}$ month. The results were recorded.

Test samples at 37° C.: The test samples were put into a thermostat at 37° C., then the above items of these samples were respectively tested in the $1^{st}$, $3^{rd}$, $6^{th}$, $9^{th}$, $12^{th}$, $18^{th}$, $24^{th}$ month. The results were recorded.

4. Results and Conclusion

1) At 37° C., according to data collected at designated points during testing and compared with data before testing, the potency began descending from the $6^{th}$ month and the changes in the three batches were similar. The appearance of other items had no changes.

2) At 25° C., according to data collected at designated points during testing and compared with data before the testing, the potency only had a little change, and the changes in the three batches were similar. The appearance of other items had no changes.

3). At 2~8° C., according to data collected at designated points during testing and compared with data before testing, the potency of the three batches all were stable. The appearance of other items also had no changes.

In conclusion, it is suggested that the lyophilized powder of recombinant super-compound interferon for injection should be better stored and transported at low temperatures. Without such conditions, the product can also be stored for short periods (i.e. 3 months) at room temperature.

EXAMPLE 3.5

Production Flow Chart of rSIFN-co

1. Production 1.1 Fermentation

Use mixture of LB+M9 as culturing medium. The amount of innoculum will be 1.5%. Agitate to OD600=0.4 (about 3.5 hours) under 32° C., then raise temperature to 42° C. Continue the agitation for another 6 hours, the expression of rSIFN-co will reach the maximum level. The examination under scanning of the gel resulting from SDS-PAGE shows that the level of expression is up to 57%, which is the highest standard in China.

1.2 Purification

Centrifuge the bacteria solution to collect the bacterial pallet

↓

Physiological saline wash for two (2) times

↓

Adding buffer (50 mM Tris-HCl, 1 mM EDTA, 100 mM NaCl, 1% Triton X-100, 1-2 M Urea), sonication to disrupt bacterial cells for 20-30 minutes

↓

Precipitate the buffer solution and wash a few times until the color turns into pure white

↓

Use 7M Guanidine HCl to denature

↓

```
                    -continued
        Dilute the Guanidine HCl to renature, stay
                        overnight
                           │
                           ▼
              Use Sephadex G25 to desalt
                           │
                           ▼
            Use 0.1 M NaCl to apply CM-Sepharose
                           │
                           ▼
         Stepwise elution to collect the active peak
                           │
                           ▼
        After the active peak is desalted, apply to HPLC
                  positively charged column
                           │
                           ▼
            Use 0.1 M NaCl in stepwise elution, collect
          active peak which is the product of rSIFN-co
                           │
                           ▼
          Add protection carrier and lyophiling agent
                           │
                           ▼
         Seperate lyophilized materials (rSIFN-co)
```

The purity of the product (rSIFN-co) from this production procedure is shown to 95% under the test of SDS-PAGE where molecular weight is 14.5 Kda. The reverse phase HPLC shows a single peak and the purity is up to 97%. Its specific activity is up to $1 \times 10^9$ IU/mg protein.

1.3 Packaging and Inspection

After HPLC purification, 2% human serum albumin, 1% sucrose and 1% glucose are added to the rSIFN-co. It is then separated and lyophilized into injection sample. When tested under the Wish-VVS inspection system, the result was $4.5 \times 10^8$ IU. When tested with aseptic inspection and pyrogen inspection under the standard requirement of China, the results were negative. This result complies with the requirements for IV injection.

2. Quality Control 2.1 Biological characteristics (1) When using LB+M9 to cultivate bacteria, the characteristics should match with the typical characteristics of *E-coli* bacteria. No other bacteria were detected.

(2) When smeared for Gram staining and inspected under a microscope, it is bacteria-negative.

(3) Reaction to antibiotics is the same as those original bacteria.

(4) Electron microscope inspection shows typical characteristics of *E-coli* bacteria. No mycoplasma, virus spore or other micro pollutes was detected.

(5) Biochemical reaction test shows characteristics of *E-coli* bacteria.

2.2 Quality control of interferon expression (1) Interferon expression (cultivated in an agitating platform) matches the amount of expression in original input bacteria.

(2) When tested with anti-interferon serum, a reaction is shown.

(3) Plasmid inspection: Restriction digest matched with the original plasmid.

2.3 Bacteria strain product

Bacteria strain product denotes the specimen from the original bacteria strain that was produced from the procedures shown in 1.2.

The bacteria strain product should be inspected as follows to make sure there is no derivation: Use LB to plate 2-3 pieces and cultivate. Separate and take 5-10 bacteria groups for the test of interferon expression. Repeat the test at least two (2) times. Only use the one which shows the highest % to be the bacteria strain product.

2.4 Innoculum

The innoculum denotes the chosen bacteria strain product after fermentation. The amount, cultivation time and most appropriate OD value of innoculum can be decided according to bacteria strain. An anti-polluted bacteria procedure should apply for whatever innoculum would be produced.

2.5 Growing of bacteria strain

Growing of bacteria strain would be done in a Bacteria Free room environment where no more than one bacterium is growing in the same room. Same culturing medium will be used for both bacteria strain and innoculum. The one used in rSIFN-co is LB.

2.6 Fermentation (1) Fermentation only takes place in a clean fermentation room with a single bacteria fermentation environment.

(2) Cleaning of fermentation container and tube is done twice, before and after the insertion of culturing medium. Then, the container should be frozen to reach the appropriate temperature for innoculum.

(3) Avoid using antibiotic which might affect cell growth in the culturing medium.

(4) Fermentation parameters like temperature, pH value, dissolved oxygen and time required could be varied according to different types of bacterial strains.

2.7 Bacteria collection (1) Centrifuge the bacteria solution to collect bacteria or use another method. All apparatus should be cleaned before and after the operation. The waste solution should be drained after the cleaning procedure.

(2) The bacteria should be kept under 4-8° C. if they are going to be split within 24 hours. Otherwise, they should be kept under −30° C. Those are kept under such conditions can be used within 6 months.

2.8 Bacteria cell lysis (1) Use appropriate buffer solution to balance the bacteria strain. Cell lysis can be done by physical, chemical or biological methods. Use centrifuge to precipitate the bacteria and apply cleaning solutions.

(2) If the chemical method is used to split cells, no solutions harmful to human beings should be used.

2.9 Purification (1) Purification will get rid of most of the non-interferon contents. In the process of purification, no toxic materials should be found if extra elements are added.

(2) If using antibody affinity chromatography for purification, there should be an indication of the source and degree of purity. Also, inspection of small quality IgG should be performed.

(3) During the process of purification, clearance of pyrogen is critical. All apparatus should be checked to eliminate this interference.

(4) The highly concentrated interferon is known as "intermediate product". After inspection and tests, add albumin to raise the concentration to 2% which is now known as "albumin intermediate product". After examination and tests, it should be kept at −30° C. and never thawed before use. This product should be used within 6 months.

(5) The albumin that is used in this process should also fulfill tests and requirements such as: negativity under RBSAG inspection and an indication of the ratio among monomer, dimer and polymer.

2.10 Production into tube product (1) Filtration: Use 0.22 µ membrane to filter the bacteria. The product should be handled with aseptic techniques. Samples should be taken to test the value of the interferon.

(2) Dilution: Dilute the albumin intermediate product with 2% diluent. No preservative should be added. The product can be lyophilized after the aseptic inspection and pyrogen inspection.

2.11 Lyophilization

The lyophilization should not affect the activity of interferon, and the water content of said lyophilite will be maintained.

2.12 Inspection

There are two types of rSIFN-co made. One is for injection and the other for topical use. The specifications for the two are different. There are intermediate products and final products for each type. In the injection type, intermediate products include purified interferon, albumin intermediate product, and bacteria free albumin intermediate product. Final product from the injection type will denote only lyophilized product. The intermediate product in the topical type denotes only purified interferon. The final product from the topical type denotes only separated packed liquid formed lyophilized products.

2.13 Packaging

There is different packaging for the injection type and the topical type.

2.14 Storage

The product should be kept at 4° C. The purification solution should not be stored in a frozen state.

2.15 Expiration

The expiration period is two (2) years after the lyophilization procedure for lyophilized products. The expiration period is 6 months after individual packing for liquidated products.

EXAMPLE 4 rSIFN-co Inhibits HBV-DNA Duplication and Secretion of HBsAg and HBeAg.

Materials

Solvent and Dispensing Method: Add 1ml saline into each vial, dissolve, and mix with MEM culture medium at different concentrations. Mix on the spot.

Control drugs: IFN-α2b (Intron A) as lyophilized powder, purchased from Schering Plough. $3 \times 10^6$ U each, mix to $3 \times 10^6$ IU/ml with culture medium; Infergen® (liquid solution), purchased from Amgen, 9 µg, 0.3 ml each, equal to $9 \times 10^6$ IU, and mix with $9 \times 10^6$ IU/ml culture medium preserve at 4° C.;

2.2.15 cell: 2.2.15 cell line of hepatoma (Hep G2) cloned and transfected by HBV DNA, constructed by Mount Sinai Medical Center.

Reagent: MEM powder, Gibco American Ltd. cattle fetal blood serum, HycloneLab American Ltd. G-418 (Geneticin); MEM dispensing, Gibco American Ltd.; L-Glutamyl, imported and packaged by JING KE Chemical Ltd.; HBsAg and HBeAg solid-phase radioimmunoassay box, Northward Reagent Institute of Chinese Isotope Ltd.; Biograncetina, Northern China Medicine; And Lipofectin, Gibco American Ltd.

Experimental goods and equipment: culture bottle, Denmark Tunclon™; 24-well and 96-well culture board, Corning American Ltd.; Carbon Dioxide hatching box, Shel-Lab American Ltd.; MEM culture medium 100 ml: 10% cattle fetal blood serum, 3% Glutamy 11%, G418 380 µg/ml, biograncetina50 U/ml.

Method:

2.2.15 cell culture: Added 0.25% pancreatic enzyme into culture box with full of 2.2.15 cell, digest at 37° C. for 3 minutes, and add culture medium to stop digest and disturb it to disperse the cells, reproduce with ratio of 1:3. They will reach full growth in 10 days.

Toxicity test: Set groups of different concentrations and a control group in which cell is not acted on with medicine. Digest cell, and dispense to a 100,000 cell/ml solution. Inoculate to 96-well culture board, 200 µl each well, culture at 37° C. for 24 h with 5% $CO_2$. Test when simple cell layer grows.

Dispense rSIFN-co to $1.8 \times 10^7$ IU/ml solution than prepare a series of solutions diluted at two-fold gradients. Add into 96-well culture board, 3 wells per concentration. Change the solution every 4 days. Test cytopathic effect by microscope after 8 days. Fully destroy as 4, 75% as 3, 50% as 2, 25% as 1, zero as 0. Calculate average cell lesion and inhibition rate of different concentrations. Calculate TC50 and TC0 according to the Reed Muench method.

$$TC50 = \text{Antilog}\left(B + \frac{50-B}{A-B} \times C\right)$$

A=log>50% medicine concentration, B=log<50% medicine concentration, C=log dilution power Inhibition test for HBeAg and HBsAg: Separate into positive and negative HBeAg and HBsAg contrast groups, cell contrast group and medicine concentration groups. Inoculate 700,000 cells/ml of 2.2.15 cell into 6-well culture board, 3 ml each well, culture at 37° C. for 24 h with 5% $CO_2$, then prepare 5 gradiently diluted solutions with 3-fold as the grade (Prepare 5 solutions, each with a different protein concentration. The concentration of Solution 2 is 3 times lower than that of Solution 1, the concentration of Solution 3 is 3 times lower than that of Solution 2, etc.) $4.5 \times 10^6$ IU/ml, $1.5 \times 10^6$ IU/ml, $0.5 \times 10^6$ IU/ml, $0.17 \times 10^6 1$ U/ml, and $0.056 \times 10^6 1$ U/ml, 1 well per concentration, culture at 37° C. for 24h with 5% $CO_2$. Change solutions every 4 days using the same solution. Collect all culture medium on the $8^{th}$ day. Preserve at −20° C. Repeat test 3 times to estimate HBsAg and HBeAg with solid-phase radioimmunoassay box (Northward Reagent Institute of Chinese Isotope Ltd.). Estimate cpm value of each well with a γ-accounting machine.

Effects calculation: Calculate cpm mean value of contrast groups and different-concentration groups and their standard deviation, P/N value such as inhibition rate, IC50 and SI.

1) Antigen inhibition rate $(\%) = \frac{A - B}{A} \times 100$

A=cpm of control group; B=cpm of test group;
2) Counting the half-efficiency concentration of the medicine $$\text{Antigen inhibition IC50} = \text{Antilog}\left(B + \frac{50 - B}{A - B} \times C\right)$$

A=log>50% medicine concentration, B=log<50% medicine concentration, C=log dilution power
3) SI of interspace-conformation changed rSIFN-co effect on HBsAg and HBeAg in 2.2.15 cell culture:

$$SI = \frac{TC50}{IC50}$$

4) Estimate the differences in cpm of each dilution degree from the control group using student t test Southern blot: (1) HBV-DNA extract in 2.2.15 cell: Culture cell 8 days. Exsuction culture medium (Separate cells from culture medium by means of draining the culture medium.). Add lysis buffer to break cells, then extract 2 times with a mixture of phenol, chloroform and isoamyl alcohol (1:1:1), 10,000 g centrifuge. Collect the supernatant adding anhydrous alcohol to deposit nucleic acid. Vacuum draw, re-dissolve into 20 μl TE buffer. (2) Electrophoresis: Add 6×DNA loading buffer, electrophoresis on 1.5% agarose gel, IV/cm, at fixed pressure for 14-18 h. (3) Denaturation and hybridization: respectively dip gel into HCl, denaturaion buffer and neutralization buffer. (4) Transmembrane: Make an orderly transfer of DNA to Hybond-N membrane. Bake, hybridize and expose with dot blot hybridization. Scan and analyze relative density with gel-pro software. Calculate inhibition rate and IC50.

Results

Results from Tables 5, 6, and 7 show: After maximum innocuous concentration exponent culturing for 8 days with 2.2.15 cell, the maxima is $9.0 \pm 0 \times 10^6$ IU/ml average inhibition rate of maximum innocuous concentration rSIFN-co to HBeAg is 46.0±5.25% (P<O. 001), IC50 is $4.54 \pm 1.32 \times 10^6$ IU/ml, SI is 3.96; rate to HBsAg is 44.8±6.6%, IC50 is $6.49 \pm 0.42 \times 10^6$ IU/ml, SI is 2.77. This shows that rSIFN-co can significantly inhibit the activity of HBeAg and HBsAg, but that the IFN of the contrast group and Infergen® cannot. It has also been proved in clinic that rSIFN-co can decrease HBeAg and HBsAg or return them to normal levels.

TABLE 5

Results of inhibition rate of rSIFN-co to HBsAg and HBeAg

| Concentration ($\times 10^4$ IU/ml) | First well | Second well | Third well | Inhibition rate First well | Inhibition rate Second well | Inhibition rate Third well | Average inhibition rate | Accumulation | 1-Accumulation | Accumulated inhibition rate |
|---|---|---|---|---|---|---|---|---|---|---|
| First batch: (rSIFN-co) Inhibition effect to HBeAg | | | | | | | | | | |
| 900 | 9026 | 8976 | 10476 | 0.436227 | 0.43935 | 0.345659 | 0.407079 | 0.945909 | 0.592921 | 0.614693546 |
| 300 | 9616 | 12082 | 10098 | 0.3993754 | 0.245347 | 0.369269 | 0.337997 | 0.5388299 | 1.254924 | 0.300392321 |
| 100 | 9822 | 16002 | 12800 | 0.386508 | 0.0005 | 0.2005 | 0.195836 | 0.200833 | 2.059088 | 0.08867188 |
| 33.33333 | 15770 | 19306 | 16824 | 0.014991 | 0 | 0 | 0.004997 | 0.0049969 | 3.054091 | 0.001633453 |
| 11.11111 | 19172 | 22270 | 18934 | 0 | 0 | 0 | 0 | 0 | 4.054091 | 0 |
| Control | Cell | 16010 | | Blank | 0 | | Dilution | 3 | IC50 | 602.74446016 |
| Inhibition effect to HBsAg | | | | | | | | | | |
| 900 | 7706 | 7240 | 7114 | 0.342155 | 0.381936 | 0.392693 | 0.372261 | 0.922258 | 0.627739 | 0.595006426 |
| 300 | 8856 | 7778 | 9476 | 0.2439816 | 0.336008 | 0.191053 | 0.257014 | 0.5499972 | 1.370724 | 0.286349225 |
| 100 | 10818 | 10720 | 10330 | 0.07649 | 0.084856 | 0.118149 | 0.093165 | 0.292983 | 2.27756 | 0.113977019 |
| 33.33333 | 10744 | 11114 | 10570 | 0.082807 | 0.051221 | 0.097661 | 0.07723 | 0.1998179 | 3.20033 | 0.058767408 |
| 11.11111 | 10672 | 9352 | 10810 | 0.088953 | 0.201639 | 0.077173 | 0.122588 | 0.122588 | 4.077742 | 0.02918541 |
| Control | Cell | 11714 | | Blank | 0 | | Dilution | 3 | IC50 | 641.7736749 |
| Second batch: (rSIFN-co) Inhibition effect to HBeAg | | | | | | | | | | |
| 900 | 7818 | 8516 | 9350 | 0.554378 | 0.514592 | 0.467054 | 0.512008 | 1.371181 | 0.487992 | 0.737521972 |
| 300 | 10344 | 10628 | 9160 | 0.4103967 | 0.394209 | 0.477884 | 0.427497 | 0.8591731 | 1.060496 | 0.447563245 |
| 100 | 12296 | 14228 | 13262 | 0.299134 | 0.18901 | 0.244072 | 0.244072 | 0.4316522 | 1.816423 | 0.19201839 |
| 33.33333 | 15364 | 17414 | 16188 | 0.124259 | 0.00741 | 0.77291 | 0.069653 | 0.1876045 | 2.74677 | 0.063933386 |
| 11.11111 | 17386 | 13632 | 15406 | 0.009006 | 0.222982 | 0.121865 | 0.117951 | 0.117951 | 3.628819 | 0.03148073 |
| Control | Cell | 16962 | | Blank | 0 | | Dilution | 3 | IC50 | 365.9357846 |
| Inhibition effect to HBsAg | | | | | | | | | | |
| 900 | 5784 | 6198 | 5792 | 0.498265 | 0.462353 | 0.497571 | 0.486063 | 0.893477 | 0.513937 | 0.634835847 |
| 300 | 7150 | 8534 | 8318 | 0.379771 | 0.259715 | 0.278452 | 0.30598 | 0.4074138 | 1.207957 | 0.252210647 |
| 100 | 9830 | 11212 | 10210 | 0.147294 | 0.027412 | 0.11433 | 0.096345 | 0.101434 | 2.111612 | 0.04583464 |
| 33.33333 | 13942 | 12368 | 13478 | 0 | 0 | 0 | 0 | 0.0050891 | 3.111612 | 0.001632835 |
| 11.11111 | 12418 | 11634 | 11352 | 0 | 0 | 0.015267 | 0.005089 | 0.005089 | 4.106523 | 0.001237728 |
| Control | Cell | | | Blank | 0 | | Dilution | 3 | IC50 | 611.0919568 |

TABLE 5-continued

Results of inhibition rate of rSIFN-co to HBsAg and HBeAg

| Concentration (×10⁴ IU/ml) | First well | Second well | Third well | First well | Second well | Third well | Average inhibition rate | Accumulation | 1-Accumulation | Accumulated inhibition rate |
|---|---|---|---|---|---|---|---|---|---|---|
| | | | | | Inhibition rate | | | | | |
| | | | | Third batch: (rSIFN-co) Inhibition effect to HBeAg | | | | | | |
| 900 | 9702 | 9614 | 8110 | 0.428016 | 0.433204 | 0.521872 | 0.461031 | 1.316983 | 0.538969 | 0.709599543 |
| 300 | 8914 | 10032 | 8870 | 0.4744723 | 0.40856 | 0.477066 | 0.453366 | 0.8559525 | 1.085603 | 0.440859127 |
| 100 | 16312 | 12688 | 13934 | 0.038321 | 0.251975 | 0.178517 | 0.156271 | 0.402586 | 1.929332 | 0.172641621 |
| 33.33333 | 15080 | 12814 | 13288 | 0.110954 | 0.244547 | 0.216602 | 0.190701 | 0.2463153 | 2.738631 | 0.082519158 |
| 11.11111 | 21928 | 15366 | 15728 | 0 | 0.094093 | 0.072751 | 0.0055615 | 0.055615 | 3.683017 | 0.014875633 |
| Control | Cell | 17544 | | Blank | 0 | | Dilution | 3 | IC50 | 382.0496935 |
| | | | | Inhibition effect to HBsAg | | | | | | |
| 900 | 5616 | 6228 | 5346 | 0.496864 | 0.442035 | 0.521054 | 0.486651 | 0.763125 | 0.513349 | 0.597838293 |
| 300 | 8542 | 8590 | 7096 | 0.234725 | 0.230425 | 0.364272 | 0.276474 | 0.2764738 | 1.236875 | 0.182690031 |
| 100 | 11420 | 11360 | 11394 | 0 | 0 | 0 | 0 | 0 | 2.236875 | 0 |
| 33.33333 | 12656 | 11582 | 13110 | 0 | 0 | 0 | 0 | 0 | | 0 |
| 11.11111 | 13142 | 12336 | 13342 | 0 | 0 | 0 | 0 | 0 | 4.236875 | 0 |
| Control | Cell | 11528 | | Blank | 0 | | Dilution | 3 | IC50 | 694.7027149 |

HBeAg: Average IC50: 450.2434 SD: 132.315479
HBsAg: Average IC50: 649.1894 SD: 42.29580

TABLE 6

Results of inhibition rate of Intron A (IFN-α2b) to HBsAg and HBeAg

| Concentration (×10⁴ IU/ml) | First well | Second well | Third well | First well | Second well | Third well | Average inhibition rate | Accumulation | 1-Accumulation | Accumulated inhibition rate |
|---|---|---|---|---|---|---|---|---|---|---|
| | | | | | Inhibition rate | | | | | |
| | | | | Inhibition effect to HBeAg | | | | | | |
| 300 | 14918 | 11724 | 9950 | 0 | 0.029711 | 0.176529 | 0.068747 | 0.068747 | 0.931253 | 0.068746724 |
| 100 | 14868 | 16890 | 15182 | 0 | 0 | 0 | 0 | 0 | 1.931253 | 0 |
| 33.33333 | 16760 | 21716 | 16400 | 0 | 0 | 0 | 0 | 0 | 2.931253 | 0 |
| 11.11111 | 20854 | 15042 | 16168 | 0 | 0 | 0 | 0 | 0 | 3.931253 | 0 |
| 3.703704 | 12083 | 12083 | 12083 | 0 | 0 | 0 | 0 | 0 | 4.931253 | 0 |
| Control | Cell | 17544 | | Blank | 0 | | Dilution | 3 | IC50 | FALSE |
| | | | | Inhibition effect to HBsAg | | | | | | |
| 300 | 9226 | 8196 | 9658 | 0.152489 | 0.247106 | 0.521054 | 0.1708 | 0.189295 | 0.8292 | 0.185857736 |
| 100 | 10946 | 10340 | 10828 | 0 | 0.050156 | 0.364272 | 0.018495 | 0.0184947 | 1.810705 | 0.010110817 |
| 33.33333 | 12250 | 12980 | 13934 | 0 | 0 | 0 | 0 | 0 | 2.810705 | 0 |
| 11.11111 | 12634 | 12342 | 12000 | 0 | 0 | 0 | 0 | 0 | 3.810705 | 0 |
| 3.703704 | 10886 | 10886 | 10886 | 0 | 0 | 0 | 0 | 0 | 4.810705 | 0 |
| Control | Cell | 10886 | | Blank | 0 | | Dilution | 3 | IC50 | FALSE |

TABLE 7

Results of inhibition rate of Infergen ® to HBsAg and HBeAg

| Concentration (×10⁴ IU/ml) | First well | Second well | Third well | First well | Second well | Third well | Average inhibition rate | Accumulation | 1-Accumulation | Accumulated inhibition rate |
|---|---|---|---|---|---|---|---|---|---|---|
| | | | | | Inhibition rate | | | | | |
| | | | | Inhibition effect to HBeAg First batch: (Infergen ®) | | | | | | |
| 900 | 14172 | 12156 | 17306 | 0.091655 | 0.220869 | 0 | 0.104175 | 0.306157 | 0.895825 | 0.254710274 |
| 300 | 13390 | 12288 | 16252 | 0.1417767 | 0.212409 | 0 | 0.118062 | 0.2019827 | 1.777764 | 0.102024519 |
| 100 | 14364 | 18834 | 14194 | 0.079349 | 0 | 0.090245 | 0.056531 | 0.083921 | 2.721232 | 0.029916678 |
| 33.33333 | 15722 | 16034 | 16340 | 0 | 0 | 0 | 0 | 0.0273897 | 3.721232 | 0.007306592 |
| 11.11111 | 17504 | 17652 | 14320 | 0 | 0 | 0.082169 | 0.02739 | 0.02739 | 4.693843 | 0.005801377 |
| Control | Cell | 15602 | | Blank | 0 | | Dilution | 3 | IC50 | FALSE |

TABLE 7-continued

Results of inhibition rate of Infergen ® to HBsAg and HBeAg

| Concentration (×10⁴ IU/ml) | First well | Second well | Third well | First well | Inhibition rate Second well | Third well | Average inhibition rate | Accumulation | 1-Accumulation | Accumulated inhibition rate |
|---|---|---|---|---|---|---|---|---|---|---|
| | | | | | Inhibition effect to HBsAg | | | | | |
| 900 | 12080 | 11692 | 12234 | 0 | 0.01275 | 0 | 0.00425 | 0.025163 | 0.99575 | 0.024647111 |
| 300 | 12840 | 11484 | 12350 | 0 | 0.030313 | 0 | 0.010104 | 0.0209125 | 1.985646 | 0.010422073 |
| 100 | 12894 | 14696 | 15086 | 0 | 0 | 0 | 0 | 0.010808 | 2.985646 | 0.003606955 |
| 33.33333 | 15032 | 12928 | 13020 | 0 | 0 | 0 | 0 | 0.0108081 | 3.985646 | 0.002704416 |
| 11.11111 | 11794 | 11984 | 11508 | 0.004137 | 0 | 0.028287 | 0.010808 | 0.010808 | 4.974837 | 0.002167838 |
| Control | Cell | 11843 | | Blank | 0 | | Dilution | 3 | IC50 | FALSE |
| | | | | | Second batch: (Infergen ®) Inhibition effect to HBeAg | | | | | |
| 900 | 6278 | 6376 | 6408 | 0.200051 | 0.187564 | 0.183486 | 0.190367 | 0.274635 | 0.809633 | 0.253290505 |
| 300 | 7692 | 9092 | 6394 | 0.0198777 | 0 | 0.18527 | 0.068383 | 0.0842678 | 1.74125 | 0.046161005 |
| 100 | 8960 | 7474 | 8190 | 0 | 0.047655 | 0 | 0.015885 | 0.015885 | 2.725365 | 0.005794856 |
| 33.33333 | 8530 | 8144 | 9682 | 0 | 0 | 0 | 0 | 0 | 3.725365 | 0 |
| 11.11111 | 7848 | 7848 | 7848 | 0 | 0 | 0 | 0 | 0 | 4.725365 | 0 |
| Control | Cell | 7848 | | Blank | 0 | | Dilution | 3 | IC50 | FALSE |
| | | | | | Inhibition effect to HBsAg | | | | | |
| 900 | 12364 | 12268 | 12274 | 0.036171 | 0.043655 | 0.043187 | 0.041004 | 0.140162 | 0.958996 | 0.12751773 |
| 300 | 11590 | 12708 | 13716 | 0.0965076 | 0.009355 | 0 | 0.035287 | 0.0991581 | 1.923709 | 0.0490186 |
| 100 | 12448 | 13468 | 13982 | 0.029623 | 0 | 0 | 0.009874 | 0.063871 | 2.913834 | 0.02144964 |
| 33.33333 | 12616 | 11346 | 12444 | 0.016526 | 0.115529 | 0.029935 | 0.053996 | 0.0539965 | 3.859838 | 0.013796309 |
| 11.11111 | 12828 | 12828 | 12828 | 0 | 0 | 0 | 0 | 0 | 4.859838 | 0 |
| Control | Cell | 12828 | | Blank | 0 | | Dilution | 3 | IC50 | FALSE |
| | | | | | Third batch: (Infergen ®) Inhibition effect to HBeAg | | | | | |
| 900 | 7240 | 6642 | 6158 | 0.064599 | 0.14186 | 0.204393 | 0.136951 | 0.217399 | 0.863049 | 0.201211735 |
| 300 | 11072 | 8786 | 6902 | 0 | 0 | 0.108269 | 0.03609 | 0.0804479 | 1.82696 | 0.042176564 |
| 100 | 7016 | 9726 | 7552 | 0.09354 | 0 | 0.024289 | 0.039276 | 0.044358 | 2.787683 | 0.015663017 |
| 33.33333 | 7622 | 8866 | 8676 | 0.015245 | 0 | 0 | 0.005082 | 0.0050818 | 3.782601 | 0.001341671 |
| 11.11111 | 7740 | 7740 | 7740 | 0 | 0 | 0 | 0 | 0 | 4.782601 | 0 |
| Control | Cell | 7740 | | Blank | 0 | | Dilution | 3 | IC50 | FALSE |
| | | | | | Inhibition effect to HBsAg | | | | | |
| 900 | 11048 | 11856 | 11902 | 0.04775 | 0 | 0 | 0.015917 | 0.015917 | 0.984083 | 0.015916796 |
| 300 | 13454 | 12896 | 11798 | 0 | 0 | 0 | 0 | 0 | 1.984083 | 0 |
| 100 | 12846 | 13160 | 12546 | 0 | 0 | 0 | 0 | 0 | 2.984083 | 0 |
| 33.33333 | 12680 | 12458 | 12360 | 0 | 0 | 0 | 0 | 0 | 3.984083 | 0 |
| 11.11111 | 11602 | 11602 | 11602 | 0 | 0 | 0 | 0 | 0 | 4.984083 | 0 |
| Control | Cell | 11602 | | Blank | 0 | | Dilution | 3 | IC50 | FALSE |

HBeAg: Average IC50: 0  SD: 0
HBsAg: Average IC50: 0  SD: 0

EXAMPLE 5

Preparation of rSIFN-co

| Preparation of lyophilized injection | |
|---|---|
| | Lyophilized powder |
| Stock Solution of rSIFN-co | 34.5 µg/ml |
| PB (pH 7.0) | 10 mmol/L |
| Glycine | 0.4 mol/L |

Preparation technique: Weigh materials according to recipe. Dissolve with sterile and pyrogen-free water. Filter through 0.22 µm membrane to de-bacterialize, preserve at 6-10° C. Fill in vials after affirming it is sterile and pyrogen-free, 0.3 ml /vial or 0.5 ml/vial, and lyophilize in freeze dryer.

| Preparation of liquid injection | |
|---|---|
| | Solution |
| Stock Solution of rSIFN-co | 34.5 µg/ml |
| PB (pH 7.0) | 25 mmol/L |
| NaCl | 0.1 mol/L |

Preparation: Weigh materials according to recipe. Add to desired level with sterile and pyrogen-free water. Filter through 0.22 µm membrane to de-bacterialize, preserve at 6-10° C. Fill in airtight vial after affirming it is sterile and non-pyrogen at 0.3 ml /vial or 0.5 ml/vial. Storage at 2-10° C., and protect from light.

EXAMPLE 6

Acute Toxicity of rSIFN-co

Treat mice with large dose (150 μg/kg, equal to 1000 times of the normal dose per kilo used in treatment of adult patients) of rSIFN-co at one time by intramuscular injection. Then, observe and record their deaths and toxic reactions. Results show that: 24 hours after injection, no abnormal reaction had been recorded. The organs of the animals which had been selected to be killed also had no signs of abnormal changes. Those remaining mice were all kept alive and were normal after two weeks. The weights of mice in the experimental group and control group all increased, and the ratio of increase had no obvious difference between the two groups (P>0.05) according to their weights on the fourteenth day. No abnormal changes were seen from the main organs of those mice after two weeks.

1. Experimental Material 1.1 Animals 40 healthy adult mice, weighing 18-22 g, half male and half female, qualified by Sichuan experiment animal control center.

1.2 Medicines rSIFN-co (Provided by Sichuan Huiyang Life-engineering Ltd.) sterilized solution, 0.15 mg/ml, Lot: 981201 rSIFN-co was administered i.m. in saline.

2. Method

Separate the 40 mice into two groups randomly, one for experimental medicine, another for control. Inject medicines or saline at the same ratio (0.1 ml/10 g) through muscle to each mouse according to which group they belong. (150 μg/kg of rSIFN-co for experimental group; and saline for control group). After injection, observe and record acute toxicity shown in mice. Kill half of the mice (male and female each half) to check whether there were any abnormal pathologic changes in their main organs, such as heart, spleen, liver, lung, kidney, adrenal gland, stomach, duodenum, etc. after 24 hours. Those that remain are kept and observed until the fourteenth day. Weigh all mice, kill them, and then observe the appearance of the organs listed above to see if there are any abnormalities. Take pathological tissue and examine it, using the examination to assess the difference in weight increases in the two groups.

3. Results

Results show that there was no acute toxicity seen after all mice were treated with i.m. rSIFN-co with 150 μg/kg at a time, equal to 1000 times the normal dose per kilo used in treatment of adult patients. In the 14 days after injection, all mice lived well. They ate, drank, exercised, and excreted normally and showed normal hair conditions. None of them died. The observation of the main organs of the randomly selected mice shows no abnormal changes 24 hours after injection. 14 days after injection, all remaining mice were killed. Autopsies also showed no changes. The weights of mice in the two groups all increased, but no obvious difference was shown when accessed with statistic method (p>0.05). See Table 8:

TABLE 8

Influence to weights of mice after injection of rSIFN-co

| Group | Dose | Animal | Weights before injection (g) | Weights after injection (g) | Increased value of weights (g) |
|---|---|---|---|---|---|
| Control | 0 | 20 | 19.8 ± 1.7 | 30.8 ± 2.8 | 11.0 ± 2.9 |
| rSIFN-co | 150 | 20 | 19.4 ± 1.7 | 32.1 ± 3.3 | 12.7 ± 4.3 |

4. Conclusion

Under conditions of this experiment, there were no toxic reactions in all mice after injection of rSIFN-co with 150 μg/kg. The conclusion can be reached that the maximum tolerable dose of i.m. in mice is 150 μg/kg, which is equal to 1000 times the normal dose per kilo used in treatment of adult patients.

EXAMPLE 7

The Clinic Effects of Recombinant Super-Compound Interferon (rSIFN-co)

The recombinant super-compound interferon (rSIFN-co) is an invention for viral disease therapy, especially for hepatitis. Meanwhile, it can inhibit the activity of EB viruses, VSV, Herpes simplex viruses, cornaviruses, measles viruses et al. Using Wish cells /VSV system as the assay for anti-virus activity, the results showed that: the other rIFN, was $0.9 \times 10^8$ IU/mg, Intron A was $2.0 \times 10^8$ IU/mg and rSIFN-co was $9 \times 10^8$ IU/mg. The anti-viral activity of rSIFN-co is much higher than those of the former two.

Under the permission of the State Food and Drug Administration (SFDA), People's Republic of China, the clinical trials have taken place in West China Hospital, Sichuan University, the Second Hospital of Chongqing Medical University, the First Hospital of School of Medical, Zhejiang University since the February 2003. The clinical treatment which focuses on hepatitis B is conducted under the guidance of the mutilcenter, double-blind random test. IFN-α1b was used as control, and the primary results showed the following:

The Effect of rSIFN-co Compared with IFN-α1b in the Treatment of Chronic Active Hepatitis B 1. Standard of patients selection: Standards 1-4 are effective for both treatment with rSIFN-co (9 μg) and IFN-α1b (5 MU, 50 μg), and Standards 1-5 are for rSIFN-co (15 μg) treatment.

1). Age: 18-65
   2). HBsAg test positive over last six months, HBeAg test positive, PCR assay, HBV-DNA copies$\geq 10^5$/ml
   3). ALT$\geq$two times the normal value
   4). Never received IFN treatment; or received the Lamivi- dine treatment but failed or relapsed
   5). Once received other IFNs (3 MU or 5 MU) treatment six months ago following the standard of SFDA, but failed or relapsed 2. Evaluation of the Effects:

In reference to the recommendations from the Tenth China National Committee of Virus Hepatitis and Hepatopathy, the effects were divided into three degrees according to the ALT level, HBV-DNA and HBeAg tests.

Response: ALT normal level, HBV-DNA negative, HBeAg negative

Partial response: ALT normal level, HBV-DNA or HBeAg negative

Non response: ALT, HBV-DNA and HBeAg unchanged

The response and partial response groups were considered effective cases.

3. Results of Clinic Trial:

TABLE 9

| Period | group | Medicine | cases | Effective Rate | HBsAg Transfer to negative rate | HBeAg Transfer to negative rate | HBV-DNA Transfer to negative rate | Heptal function Recover rate |
|---|---|---|---|---|---|---|---|---|
| 8-12 week | A | rSIFN-co (9 µg) | 32 | 46.88 (15) | 9.38 (3) | 28.12 (9) | 37.50 (12) | 84.38 (27) |
| | B | IFN-α1b (5 MU, 50 µg) | 32 | 21.88 (7) | 0.00 (0) | 9.38 (3) | 15.62 (5) | 56.25 (18) |
| 16-24 week | A | rSIFN-co (9 µg) | 64 | 54.69 (35) | 7.81 (5) | 25.00 (16) | 34.38 (22) | 90.62 (58) |
| | B | IFN-α1b (5 MU, 50 µg) | 64 | 25.00 (16) | 0.00 (0) | 9.38 (6) | 18.75 (12) | 78.13 (50) |

Group A: treatment with rSIFN-co (9 µg)
Group B: treatment with IFN-α1b (5 MU, 50 µg)

In Group C, the cases were chronic active hepatitis B treatment with other IFNs (3 MU or 5 MU) before but failed or relapsed and treated with rSIFN-co (15 µg), subcutaneous injection, every one day, last 24 weeks. The total cases are 13. After 12 weeks treatment, 7 of 13 (53.85%) were effective. 3 of 13 (23.08%) HBeAg transferred to negative; 7 of 13(53.85%) HBV-DNA transferred to negative; 11 of 13 (84.62%) hepal functions recovered to normal.

4. The Side Effects of rSIFN-co Compared with IFN-α1b in the Treatment

The side effects of IFN include fever, nausea, myalgia, anorexia, hair loss, leucopenia and thrombocytopenia, etc. The maximum dose of IFN-α1b is 5 MIU per time; the routine dose is 3 MIU. When taken the routine dose, 90% patients have I-II degree (WHO standard) side effects. They are fever lower than 38° C., nausea, myalgia, anorexia, etc. When taken at maximum dose, the rate of side effects do not rise obviously, but are more serious. The maximum dose of rSIFN-co is 24 µg, subcutaneous injection, every one day for 3 months. The routine dose is 9 µg. When routine doses were used, less than 50% patients have I-II degree (WHO standard) side effects, including fever below 38° C., nausea, myalgia, anorexia, leucopenia and thrombocytopenia slightly. With maximum dosage, about 50% patients suffered from leucopenia and thrombocytopenia after using rSIFN-co one month, but those side effects would disappear after stopping treatment for one week. It is safe for continued use.

Observations of rSIFN-co Treatment of Hepatitis C

1. Standard of patient selection
  1. Age: 18-65
  2. HCV antibody positive
  3. ALT≧1.5 times of the normal value, last more than 6 months
2. Evaluation of the effects:
Referring to the standard of Infergen® (interferon alfacon-1) for treatment of hepatitis C and according to the ALT level and HCV-RNA test, divided the effects into three degree:
  Response: ALT normal level, HCV-RNA negative
  Partial response: ALT normal level, HCV-RNA unchanged
  Non response: ALT and HCV-RNA unchanged.
3. Effects in clinic The clinical trial was done at the same time with hepatitis B treatment. 46 cases received the treatment, 9 µg each time, subcutaneous injection, every day for 24 weeks. After treatment, 26 of 46 (56.52%) have obvious effects, 12 of 46 (26.08%) HCV-RNA transferred to negative, 26 of 46 (56.52%) hepal functions recovered to normal.

EXAMPLE 8

Comparison of Inhibitory Effects of Different Interferons on HBV Gene Expression Hepatitis B virus (HBV) DNA contains consensus elements for transactivating proteins whose binding activity is regulated by interferons. Treatment of HBV-infected hepatocytes with interferons leads to inhibition of HBV gene expression. The aim of the present study was to characterize the effects of different interferons on HBV regulated transcription. Using transient transfection of human hepatoma cells with reporter plasmids containing the firefly luciferase gene under the control of HBV-Enhancer (EnH) I, Enh II and core promoter, Applicant studied the biological activities of three different interferons on transcription.

Materials and Methods

1. Interferons: IFN-con1 (INFERGEN®), IFN-Hui-Yang (rSIFN-co) and IFN-beta 1b

2. Reporter plasmid: The DNA fragments containing HBV-Enhancer (EnH) I, Enh II and core promoter were prepared using PCR and blunt-end cloned into the Smal I site of the promoter- and enhancer-less firefly luciferase reporter plasmid pGL3-Basic (Promega, Wis., USA). The resulting reporter plasmid was named as pGL3-HBV-Luc.

3. Cell Culture and DNA transfection: HepG2 cells were cultured in DMEM medium supplemented with 10% FBS and 100 U/ml penicillin and 100 ug/ml streptomycin. The cells were kept in 30° C., 5% CO2 incubator. The cells were transfected with pGL3-HBV-Luc reporter plasmid using Boehringer's Lipofectin transfection kit. After 18 hours, the medium containing transfection reagents was removed and fresh medium was added with or without interferons. The cells were kept in culture for another 48 hours.

4. Luciferase Assay: Forty-eight hours after addition of interferon, the cells were harvested and cell lysis were prepared. The protein concentration of cell lysates were measured using Bio-Rad Protein Assay kit. The luciferase activity was measured using Promega's Luciferase Reporter Assay Systems according to the instructions of manufacturer.

Results

Expression of Luciferase Activity in Different Interferon—Treated Cell Lysates

TABLE 10

| No treatment | IFN-con1 | IFN-Hui-Yang | IFN-beta 1b |
|---|---|---|---|
| 100 | 48 + 8 | 29 + 6 | 64 + 10 |

This result shows that γSIFN-co inhibits most effectively on the expression of HBV gene expression.

EXAMPLE 9

Side Effects and Changes in Body Temperature when Using γSIFN-co

There are usually more side effects to using interferon. The side effects includes: nausea, muscle soreness, loss of appetite, hair loss, hypoleucocytosis (hypoleukmia; hypoleukocytosis; hypoleukia), and decrease in blood platelets, etc.

Method

Sample patients are divided into two groups. 11 patients in Group A were injected with 9 μg INFERGEN®. 10 patients in Group B were injected with 9 μg rSIFN-co. Both groups were monitored for 48 hours after injections. First monitoring was recorded 1 hour after injection, after that, records were taken every 2 hours.

Table 11 is the comparison of side effects between patients being injected with 9 μg of Infergen® and 9 μg of γSIFN-co.

TABLE 11

| | | Side Effects | |
|---|---|---|---|
| | | γSIFN-co 9 μg Person: n = 10 Headcount | Infergen ® 9 μg Person: n = 11 Headcount |
| Body Systems | Reactions | | |
| In General | Feebleness | 3 | 3 |
| | Sole Heat | 1 | |
| | frigolability | 3 | 4 |
| | Lack of strength in legs | | 3 |
| | Mild lumbago | 2 | 1 |
| | Body soreness | 4 | 5 |
| Central Nervous System/Peripheral Nervous System | Headache | 3 | 6 |
| | Dizziness | 2 | 11 |
| | Drowsiness | | 3 |
| Gastroenterostomy | Apoclesis | 1 | |
| | Celiodynia | 1 | |
| | Diarrhea | 1 | |
| Musculoskeletal system | Myalgia | 1 | 2 |
| | Arthralgia | 2 | |
| Respiratory system | Stuffy nose | 1 | |
| Paropsia | Swollen Eyes | | 1 |

Result

For those patients who were injected with rSIFN-co, the side effects were minor. They had some common symptoms similar to flu, such as: headache, feebleness, frigolability, muscle soreness, hidrosis, arthralgia (arthrodynia; arthronalgia). The side effects of those patients whom were injected with INFERGEN® were worse than those injected with rSIFN-co.

From FIGS. 8A-1, 8A-2, 8B-1, and 8B-2, it was obvious that the body temperatures of sample patients in Group A were higher than the patients in Group B. It also reflected that the endurance of rSIFN-co was much better than INFERGEN®.

EXAMPLE 10

Crystal Growth of γSIFN-co and Test of Crystallography Parameter

Crystal γSIFN-co. Two types of crystal were found after systematically trial and experiment. (See FIGS. 9-11)

1. Crystal Growth

Dissolve γSIFN-co protein with pure water (H2O) to 3 mg/ml in density. Search of crystallization by using Hampton Research Crystal Screen I and II which was made by Hampton Company. By using Drop Suspension Diffusion Method, liquid 500 μl drop 1 μl protein+1 μl liquid, in 293K temperature. First 2 different types of small crystals were found as listed in Table 12.

TABLE 12

| | Screen of γSIFN-co Crystallin | |
|---|---|---|
| Condition | I | II |
| Diluent | 0.1 M Tris-HCl PH = 8.75 | 0.1 M HEPES PH = 7.13 |
| Precipitant | 17.5% (w/v) PEG550 MME | 10% (w/v) PEG6K |
| Additives | 0.1M NaCl | 3% (v/v) MPD |
| Temperature | 293 K. | 293 K. |
| Crystal Size (mm) | 0.2 × 0.2 × 0.1 | 0.6 × 0.02 × 0.02 |
| Crystallogram | FIG. 9 | FIG. 10 |

2. Data Collection and Processing

Crystal I was used to collect X-Ray diffraction data and preliminary analysis of crystallography. Parameters were also tested. The diffraction data was collected under the room temperature. The Crystal I (Condition I) was inserted into a thin siliconized wall tube. Using BrukerAXS Smart CCD detector, the light source is CuKα (λ=1.5418Å) generated by Nonius FR591 X-ray generator. Light power 2000 KW (40 kv×50 mA), wave length 1.00Å, under explosion 60 second, Δφ=2°, the distance between crystal and detector was 50 mm. Data was processed using Proteum Procedure Package by Bruker Company. See FIG. 11 for crystal diffraction pattern (partially). See Table 13 for the result of the process.

TABLE 13

| Results of Crystallography Parameters | |
|---|---|
| Parameters | |
| a (Å) | 82.67 |
| b (Å) | 108.04 |
| c (Å) | 135.01 |
| α (°) | 90.00 |
| β (°) | 90.00 |
| γ (°) | 98.35 |
| Space Group | P2 or P2$_1$ |
| Sharpness of separation | 5 Å |
| Asymmetric molecule # | 10 |
| Dissolution | 57.6% |

In addition, there was no crystal growth of γSIFN-co based on previous publications. The closest result to the γSIFN-co was huIFN-a2b but the screen was very complicated. After seeding 3 times, crystal grew to 0.5×0.5×0.3 mm, sharpness of separation was 2.9 Å, space group was P2$_1$. The crystals were also big, asymmetric molecule number was 6, and dissolution was about 60%.

What is claimed is:

1. An artificial gene comprising the nucleotide sequence of SEQ ID NO:1, wherein said nucleotide sequence encodes a recombinant interferon having the amino acid sequence of SEQ ID NO:2.

2. A vector comprising the gene of claim 1.

3. An expression system comprising the vector of claim 2.

4. An isolated host cell comprising the vector of claim 2.

5. A process for production of a recombinant interferon comprising introducing the artificial gene of claim 1 into an appropriate host, culturing said introduced host in an appropriate condition for the expression of said interferon and harvesting the expressed interferon.

6. The process for production of claim 5, comprising extraction of the interferon from fermentation broth, collection of inclusion body, denaturation and renaturation of the harvested protein.

7. The process of claim 5, comprising separation and purification of the interferon.

8. The process of claim 5, comprising lyophilization of the purified interferon.

* * * * *

UNITED STATES PATENT AND TRADEMARK OFFICE
CERTIFICATE OF CORRECTION

PATENT NO. : 7,585,647 B2 Page 1 of 1
APPLICATION NO. : 10/928956
DATED : September 8, 2009
INVENTOR(S) : Wei It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by 309 days.

Delete the phrase "by 309 days" and insert -- by 365 days --

Signed and Sealed this

Fifteenth Day of June, 2010

David J. Kappos
*Director of the United States Patent and Trademark Office*